US007709225B2

(12) United States Patent
Wallace et al.

(10) Patent No.: US 7,709,225 B2
(45) Date of Patent: *May 4, 2010

(54) NUCLEIC ACIDS ENCODING MUTATIONS IN SODIUM CHANNELS RELATED TO EPILEPSY

(75) Inventors: Robyn Heather Wallace, Sherwood (AU); John Charles Mulley, Firle (AU); Samuel Frank Berkovic, Caulfield North (AU)

(73) Assignee: Bionomics Limited, Thebarton (AU)

( * ) Notice: Subject to any disclaimer, the term of this patent is extended or adjusted under 35 U.S.C. 154(b) by 297 days.

This patent is subject to a terminal disclaimer.

(21) Appl. No.: 11/262,647

(22) Filed: Oct. 31, 2005

(65) Prior Publication Data
US 2006/0252121 A1 Nov. 9, 2006

Related U.S. Application Data

(63) Continuation-in-part of application No. 10/451,126, filed as application No. PCT/AU01/01648 on Dec. 20, 2001, now Pat. No. 7,078,515, application No. 11/262,647, which is a continuation-in-part of application No. 10/482,834, filed as application No. PCT/AU02/00910 on Jul. 8, 2002, application No. 11/262,647, which is a continuation-in-part of application No. PCT/AU2004/001051, filed on Aug. 6, 2004.

(30) Foreign Application Priority Data

| Jul. 18, 2001 | (AU) | ........................... PS6452 |
| Mar. 5, 2002 | (AU) | ........................... PS0910 |
| May 13, 2002 | (AU) | ........................... PS2292 |
| Aug. 7, 2003 | (AU) | ........................... 2003904154 |

(51) Int. Cl.
C07H 21/04 (2006.01)
C12P 21/02 (2006.01)
C12N 15/12 (2006.01)
C12N 15/00 (2006.01)
C12N 1/21 (2006.01)
C12N 1/19 (2006.01)

(52) U.S. Cl. .............. 435/69.1; 435/320.1; 435/252.3; 435/254.2; 536/23.5

(58) Field of Classification Search ............ None
See application file for complete search history.

(56) References Cited

U.S. PATENT DOCUMENTS

| 7,078,515 B2 | 7/2006 | Wallace et al. |
| 7,282,336 B2 | 10/2007 | Wallace et al. |
| 2004/0096886 A1* | 5/2004 | Rouleau et al. ............... 435/6 |
| 2004/0229257 A1* | 11/2004 | Petrou et al. ............... 435/6 |

FOREIGN PATENT DOCUMENTS

WO    WO 01/38564    5/2001
WO    03/008574 *    1/2003

OTHER PUBLICATIONS

Chou et al., "The lack of association between febrile convulsions and polymorphisms in SCN1A," Epilepsy Research, vol. 54, pp. 53-57 (2003).
Communication pursuant to Rule 46(1) EPC corresponding to European Application No. 04718885.9-2402 PCT/AU2004000295 dated Jul. 14, 2006.
DePalma A., "Capturing Proteins Using Antibody Arrays," from Genomics and Proteomics, available online from author at www.adeplama.com, pp. 1-5.
Fukuma G., "Mutations of neuronal voltage-gated Na+ channel alpha 1 subunit gene SCN1A in core severe myoclonic epilepsy in infancy (SMEI) and in borderline SMEI (SMEB)," Epilepsia, vol. 45, No. 2, pp. 140-148 (Feb. 2004).
Goldsby et al., Immunology, Fifth Edition, section "Cross-Reactivity," p. 141.
Hirschhorn et al., "A Comprehensive Review of Genetic Association Studies," Genetics in Medicine, vol. 4, No. 2, pp. 45-61 (2002).
Kimura K., "A missense mutation in SCN1A in brothers with severe myoclonic epilepsy in infancy (SMEI) inherited from a father with febrile seizures," Brain Dev., vol. 27, No. 6, pp. 424-430 (Sep. 2005).
Lucentini J, "Gene Association Studies Typically Wrong," The Scientist, Dec. 20, 2004, p. 20.
Notice of Allowance corresponding to U.S. Patent No. 7,282,336 dated Jun. 18, 2007.
Hille 1992. Ionic Channels of Excitable Membranes, 2nd Edition, pp. 423 and 434-444.*
Lo et al. 1998. Protein Engineering 11:495-500.*
Abstracts of Decisions. Decision of a Delegate of the Commissioner of Patents corresponding to an Australian Patent Application No. 18465/01 issued Jan. 29, 2007.
Harkin et al. The spectrum of SCN1A-related infantile epileptic encephalopathies. Brain, vol. 130, (2007), pp. 843-852.
Claes et al. De novo mutations in the sodium-channel gene SCN1A cause severe myoclonic epilepsy of infancy. American Journal of Human Genetics, vol. 68, (2001), pp. 1327-1332.
Escayg et al. Mutations of SCN1A, encoding a neutomal sodium channel, in two families with GEFS+2. Nature Genetics, vol. 24, (2000), pp. 343-345.
Sugawara et al. Frequent mutations of SCN1A in severe myoclonic epilepsy in infancy. Neurology, vol. 58, No. 7, (2002).
Nabbut et al. Spectrum of SCN1A mutations in severe myoclonic epilepsy of infancy. Neurology, vol. 60, (2003), pp. 1961-1967.
European Patent Office Search Report dated Apr. 10, 2007 for European Patent Application No. 07075566.5-2401.
Stafstrom et al., "Epilepsy genes: the link between molecular dysfunction and pathophysiology," Mental Retardation and Developmental Disabilities Research Reviews, 2000, vol. 6, No. 4, 2000, pp. 281-292 XP002313392, ISSN: 1080-4013.

(Continued)

Primary Examiner—Daniel E. Kolker
(74) Attorney, Agent, or Firm—Jenkins, Wilson, Taylor & Hunt, P.A.

(57) ABSTRACT

An isolated nucleic acid molecule encoding a mutant alpha subunit of a mammalian voltage-gated sodium channel, wherein a mutation event selected from the group consisting of point mutations, deletions, insertions and rearrangements has occurred and said mutation event disrupts the functioning of an assembled sodium channel comprising this mutated subunit so as to produce an epilepsy phenotype, with the proviso that the mutation event is not a C2624T transition or a G4943A transition.

12 Claims, 8 Drawing Sheets

OTHER PUBLICATIONS

Notice of Allowance corresponding to U.S. Patent No. 7,078,515 dated Aug. 30, 2005.

Notification Concerning Transmittal of International Preliminary Report on Patentability for International Application No. PCT/AU2006/000841 dated Jan. 3, 2008.

Official Action of U.S. Patent and Trademark Office for U.S. Appl. No. 10/482,834 dated Aug. 2, 2007.

Official Action of U.S. Patent and Trademark Office for U.S. Appl. No. 10/482,834 dated Apr. 4, 2008.

Official Action of U.S. Patent and Trademark Office for U.S. Appl. No. 10/806,689 dated Nov. 29, 2006.

Thisted RA, "What is a P-value?" May 25, 1998, available online from www.stat.uchicago.edu, pp. 1-6.

Official Action corresponding to U.S. Appl. No. 10/806,899 dated Aug. 19, 2008.

Wallace R., "A Plethora of SCN1A Mutations: What Can They Tell Us?" Epilepsy Curro., vol. 5, No. 1, pp. 17-20 (Jan. 2005).

Office Communication corresponding to U.S. Appl. No. 10/482,834 dated Dec. 30, 2008.

Official Communication corresponding to U.S. Appl. No. 11/263,326 (Patent No. 7,282,336) dated Oct. 6, 2006.

Official Communication corresponding to U.S. Appl. No. 10/482,834 dated Aug. 7, 2009.

Interview Summary corresponding to U.S. Appl. No. 10/806,899 dated Oct. 8, 2009.

* cited by examiner

| | | |
|---|---|---|
| ⊘ febrile seizures (FS) | X | D188V |
| ⊘ febrile seizures plus (FS+) | Y | V1353L |
| ● FS+, extended phenotype | Z | I656M |
| ⊕ Unclassified | 0 | no mutation |
| ⦀ Partial epilepsy | | |
| ⊜ Juvenile myoclonic epilepsy | | |

Figure 3 i) D188V

| | | | | | | | | | | |
|---|---|---|---|---|---|---|---|---|---|---|
| SCN1A    | F | T | F | L | R | D | P | W | N | W | L |
| RAT SCN1A | - | - | - | - | - | - | - | - | - | - | - |
| SCN2A    | - | - | - | - | - | - | - | - | - | - | - |
| SCN3A    | - | - | - | - | - | - | - | - | - | - | - |
| SCN4A    | - | - | - | - | - | - | - | - | - | - | - |
| SCN5A    | - | - | - | - | - | - | - | - | - | - | - |
| SCN6A    | - | S | - | - | G | - | - | - | - | - | - |
| SCN8A    | - | - | - | - | - | - | - | - | - | - | - |
| SCN9A    | - | - | - | - | - | - | - | - | - | - | - |
| SCN10A   | - | - | Y | - | - | - | - | - | - | - | - |
| SCN11A   | - | S | - | - | - | - | - | - | - | - | - |
| SCN12A   | - | S | - | - | - | - | - | - | - | - | - |
| EL. EEL  | - | - | - | - | - | - | - | - | - | - | - |
| DROS     | - | - | Y | - | - | - | A | - | - | - | - |
| SQUID    | - | - | Y | - | - | - | A | - | - | - | - |
| FLATWORM | - | - | Y | - | - | S | I | - | - | - | - |
| JELLYFISH| Y | S | Y | - | - | N | S | - | - | - | - | ii) V1353L

| | | | | | | | | | | |
|---|---|---|---|---|---|---|---|---|---|---|
| SCN1A    | M | N | V | L | L | V | C | L | I | F | W |
| RAT SCN1A | - | - | - | - | - | - | - | - | - | - | - |
| SCN2A    | - | - | - | - | - | - | - | - | - | - | - |
| SCN3A    | - | - | - | - | - | - | - | - | - | - | - |
| SCN4A    | - | - | - | - | - | - | - | - | - | - | - |
| SCN5A    | - | - | - | - | - | - | - | - | - | - | - |
| SCN6A    | L | - | - | F | - | - | - | - | M | I | - |
| SCN8A    | - | - | - | - | - | - | - | - | - | - | - |
| SCN9A    | - | - | - | - | - | - | - | - | - | - | - |
| SCN10A   | - | - | - | - | - | - | - | - | - | - | - |
| SCN11A   | L | - | - | - | - | - | - | - | - | - | - |
| SCN12A   | L | - | - | - | - | - | - | - | - | - | - |
| EL. EEL  | - | - | - | - | - | - | - | - | - | - | - |
| DROS     | F | - | - | - | - | - | - | - | - | - | - |
| SQUID    | F | - | - | - | - | - | - | - | V | - | - |
| FLATWORM | F | - | - | M | V | - | - | - | V | - | - |
| JELLYFISH| A | - | - | - | - | - | - | G | V | - | - | iii) I1656M

| | | | | | | | | | | |
|---|---|---|---|---|---|---|---|---|---|---|
| SCN1A    | K | G | A | K | G | I | R | T | L | L | F |
| RAT SCN1A | - | - | - | - | - | - | - | - | - | - | - |
| SCN2A    | - | - | - | - | - | - | - | - | - | - | - |
| SCN3A    | - | - | - | - | - | - | - | - | - | - | - |
| SCN4A    | R | - | - | - | - | - | - | - | - | - | - |
| SCN5A    | R | - | - | - | - | - | - | - | - | - | - |
| SCN6A    | - | - | P | - | V | F | H | N | - | M | L |
| SCN8A    | - | - | - | - | - | - | - | - | - | - | - |
| SCN9A    | - | - | - | - | - | - | - | - | - | - | - |
| SCN10A   | R | A | - | - | - | - | - | - | - | - | - |
| SCN11A   | R | A | - | - | - | - | - | - | - | - | - |
| SCN12A   | R | A | - | - | - | - | - | - | - | - | - |
| EL. EEL  | - | - | - | - | - | - | - | - | - | - | - |
| DROS     | - | - | - | - | - | - | - | - | - | - | - |
| SQUID    | - | S | - | - | - | - | - | - | - | - | - |
| FLATWORM | - | S | - | R | - | - | - | - | - | - | - |
| JELLYFISH| D | - | - | - | - | - | - | Q | - | - | - |

Figure 6
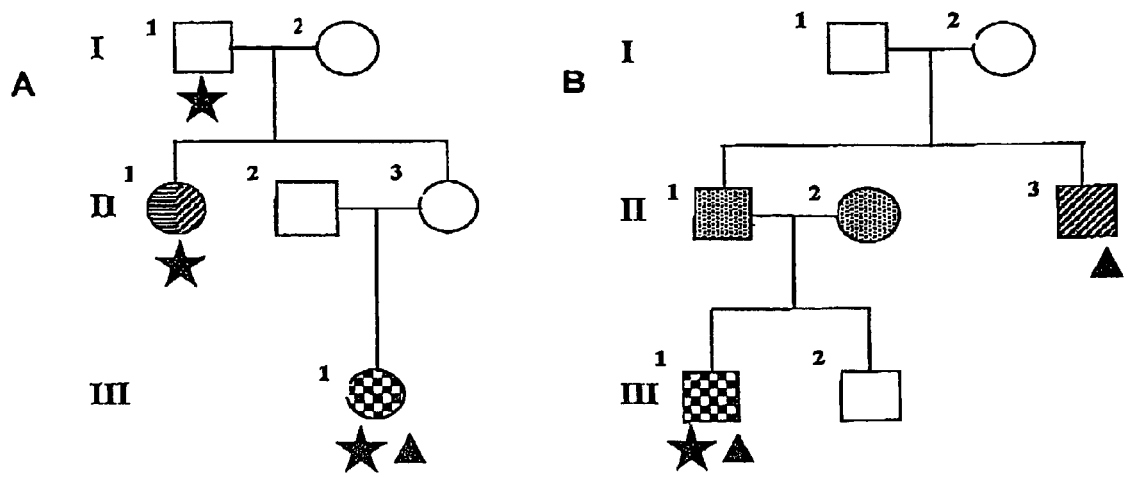
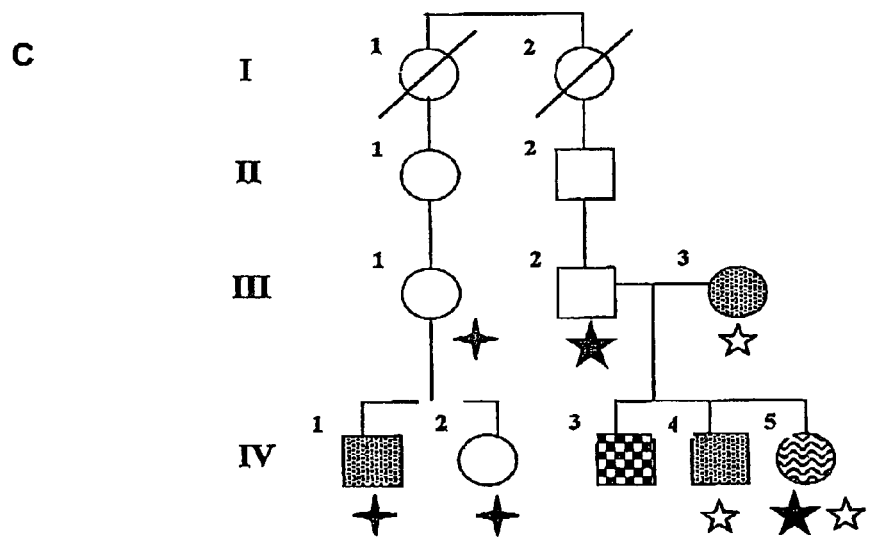
| | |
|---|---|
| ▦ Febrile Seizures | |
| ▨ Febrile Seizures Plus | ▲ A1067T SCN1A |
| ▩ Myoclonic Astatic Epilepsy | ★ N43del SCN3A |
| ≡ Absences | ✦ G1050S SCN8A |
| 〰 Severe Myoclonic Epilepsy of Infancy | ☆ Q351X GABRG2 | ns
NUCLEIC ACIDS ENCODING MUTATIONS IN SODIUM CHANNELS RELATED TO EPILEPSY

PRIORITY APPLICATION INFORMATION

This application is a continuation-in-part of U.S. patent application Ser. No. 10/451,126 filed Oct. 8, 2003 now U.S. Pat. No. 7,078,515, which corresponds to PCT Application No. PCT/AU01/01648, filed Dec. 20, 2001, which claims the benefit of PR2203 filed Dec. 20, 2000. This application is also a continuation-in-part of U.S. patent application Ser. No. 10/482,834 filed Oct. 12, 2004, which corresponds to PCT Application No. PCT/AU02/00910 filed Jul. 8, 2002, which claims the benefit of PS6452 filed Jul. 18, 2001, PSO910 filed Mar. 5, 2002, and PS2292 filed May 13, 2002. This application is also a continuation-in-part of International Application No. PCT/AU2004/001051, filed Aug. 6, 2004, which claims the benefit of AU2003904154, filed Aug. 7, 2003. The disclosure of U.S. patent application Ser. No. 10/451,126, U.S. patent application Ser. No. 10/482,834, and International Application No. PCT/AU2004/001051 are each incorporated herein by reference in their entireties.

TECHNICAL FIELD

The present invention relates to mutations in the α-subunit of mammalian voltage-gated sodium channels which are associated with idiopathic epilepsies and other disorders such as myotonias and cardiac arrhythmias, and to polymorphisms in the gene encoding the α-subunit (SCN1A).

SEQUENCE LISTING PROVIDED ON CD-R

The Sequence Listing associated with the instant disclosure has been submitted as a 0.95 MB file on CD-R (in duplicate) instead of on paper. Each CD-R is marked in indelible ink to identify the Applicants, Title, File Name (Updated FP22576.ST25.txt), Creation Date (Oct. 31, 2005), Computer System (IBM-PC/MS-DOS/MS-Windows), and Docket No. (1386/13/2). The Sequence Listing submitted on CD-R is hereby incorporated by reference into the instant disclosure.

BACKGROUND ART

Generalised epilepsy with febrile seizures plus (GEFS+; MIM 604236) was first described by Scheffer and Berkovic (1997) and is now recognised as a common epilepsy syndrome (Singh et al. 1999; Baulac et al. 1999; Moulard et al. 1999; Peiffer et al. 1999; Scheffer et al. 2000). Although GEFS+ is familial, it was initially difficult to recognise it as a distinct syndrome, because of clinical heterogeneity within each family. The common phenotypes are typical febrile seizures (FS) and febrile seizures plus (FS+); FS+ differs from FS in that the attacks with fever continue beyond age 6 years and/or include afebrile tonic-clonic seizures. Less common phenotypes include FS+ associated with absences, myoclonic or atonic seizures, and even more-severe syndromes such as myoclonic-astatic epilepsy. That such phenotypic diversity could be associated with the segregation of a mutation in a single gene was established with the identification of a mutation in the voltage gated sodium channel β1 subunit gene (SCN1B) (Wallace et al. 1998). This mutation (C121W) changes a conserved cysteine residue, disrupting a putative disulfide bridge, which results in in vitro loss of function of the β1 subunit. Without a functional β1 subunit the rate of inactivation of sodium channel α-subunits decreases, which may cause increased sodium influx, resulting in a more depolarised membrane potential and hyperexcitability. Modifier genes or the environment may interact with the SCN1B gene to account for clinical heterogeneity, but the rarity of SCN1B mutations (Wallace et al. 1998) strongly suggested additional genes of large effect underlie GEFS+ in other families (Singh et al. 1999).

GEFS+ in four families has been mapped to chromosome 2q (Baulac et al. 1999; Moulard et al. 1999; Peiffer et al. 1999; Lopes-Cendes et al. 2000). Recently, mutations in the neuronal voltage gated sodium channel alpha-1 (SCN1A) subunit were described in two GEFS+ families (Escayg et al. 2000). The mutations (T875M and R1648H) are located in highly conserved S4 transmembrane segments of the channel which are known to have a role in channel gating. It was suggested that these mutations may reduce the rate of inactivation of SCN1A and therefore have a similar effect as the β1-subunit mutation.

GEFS+ is clearly a common complex disorder, with a strong genetic basis, incomplete penetrance and genetic and phenotypic heterogeneity. Febrile seizures occur in 3% of the population, and thus this phenotype may occur sporadically in GEFS+ families, in addition to occurring as a result of the GEFS+ gene (Wallace et al 1998). Also, although some families segregate an autosomal dominant gene of major effect, in many cases clinical genetic evidence, such as bilineality, suggests that for some small families the disorder is multifactorial (Singh et al 1999). Despite this, large families continue to be ascertained and with critical phenotypic analysis, they provide opportunities to localise and ultimately identify the genes involved.

DISCLOSURE OF THE INVENTION

As used herein, the terms "mutation", "mutation event", or "mutant" is taken to mean a change in the nucleotide sequence or amino acid sequence composition of a gene when compared to the corresponding wild-type sequence. In the context of the present invention, these terms may include any change in the sequence composition, including polymorphisms and rare vartiations as disclosed herein, which give rise to an epilepsy phenotype.

The present inventors have identified new mutations in the alpha subunit of the voltage-gated sodium channel that are associated with epilepsy, in particular generalized epilepsy with febrile seizures plus (GEFS+).

According to one aspect of the present invention there is provided an isolated DNA molecule encoding a mutant alpha subunit of a mammalian voltage-gated sodium channel, wherein a mutation event selected from the group consisting of point mutations, deletions, insertions and rearrangements has occurred and said mutation event disrupts the functioning of an assembled sodium channel so as to produce an epilepsy phenotype, with the proviso that the mutation event is not a C2624T transition or a G4943A transition and the DNA molecule does not have the nucleotide sequence set forth in SEQ ID NO: 3 or SEQ ID NO: 5.

Preferably said mutation event is a point mutation.

Typically the mutation event occurs in an intracellular loop, preferably in the intracellular loop between transmembrane segments 2 and 3 of domain I, in the S4 segment of domain IV at amino acid position 1656, or in an S5 segment of a transmembrane domain. Preferably the mutation creates a phenotype of generalised epilepsy with febrile seizures plus.

In one form of the invention the mutation is in exon 4 of SCN1A and results in replacement of a highly conserved aspartic acid residue with a valine residue at amino acid position 188. The D188V mutation lies in the intracellular loop just outside the S3 segment of domain I of SCN1A and occurs as a result of an A to T nucleotide substitution at position 563 of the SCN1A coding sequence as shown in SEQ ID NO:1.

In a further form of the invention the mutation is in exon 21 of SCN1A and results in the replacement of a highly conserved valine residue with a leucine residue at amino acid position 1353. The V1353L mutation is located in the S5 segment of domain III of SCN1A and occurs as a result of a G to C nucleotide substitution at position 4057 of the SCN1A coding sequence as shown in SEQ ID NO:3.

In a still further form of the invention the mutation is in exon 26 of SCN1A and results in the replacement of a highly conserved isoleucine residue with a methionine residue at amino acid position 1656. The I1656M mutation is located in the S4 segment of domain IV of SCN1A and occurs as a result of a C to G nucleotide substitution at position 4968 of the SCN1A coding sequence as shown in SEQ ID NO:5.

In addition, the polymorphisms identified in Table 3 (SEQ ID Numbers:7-9 and 11) and the nucleic acid molecules recited in Table 4 (SEQ ID NOs:89-97, 108, 111-114, 136-144, and 153-154) form part of the invention.

The present invention also encompasses DNA molecules in which one or more additional mutation events selected from the group consisting of point mutations, deletions, insertions and rearrangements have occurred. Any such DNA molecule will have the mutation associated with epilepsy described above and will be functional, but otherwise may vary significantly from the DNA molecules set forth in SEQ ID NO:1, 3 and 5, Table 3 and Table 4.

The nucleotide sequences of the present invention can be engineered using methods accepted in the art for a variety of purposes. These include, but are not limited to, modification of the cloning, processing, and/or expression of the gene product. PCR reassembly of gene fragments and the use of synthetic oligonucleotides allow the engineering of the nucleotide sequences of the present invention. For example, oligonucleotide-mediated site-directed mutagenesis can introduce further mutations that create new restriction sites, alter expression patterns and produce splice variants etc.

As a result of the degeneracy of the genetic code, a number of polynucleotide sequences, some that may have minimal similarity to the polynucleotide sequences of any known and naturally occurring gene, may be produced. Thus, the invention includes each and every possible variation of a polynucleotide sequence that could be made by selecting combinations based on possible codon choices. These combinations are made in accordance with the standard triplet genetic code as applied to the polynucleotide sequences of the present invention, and all such variations are to be considered as being specifically disclosed.

The DNA molecules of this invention include cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages. In some instances it may be advantageous to produce nucleotide sequences possessing a substantially different codon usage than that of the polynucleotide sequences of the present invention. For example, codons may be selected to increase the rate of expression of the peptide in a particular prokaryotic or eukaryotic host corresponding with the frequency that particular codons are utilized by the host. Other reasons to alter the nucleotide sequence without altering the encoded amino acid sequences include the production of RNA transcripts having more desirable properties, such as a greater half-life, than transcripts produced from the naturally occurring mutated sequence.

The invention also encompasses production of DNA sequences of the present invention entirely by synthetic chemistry. Synthetic sequences may be inserted into expression vectors and cell systems that contain the necessary elements for transcriptional and translational control of the inserted coding sequence in a suitable host. These elements may include regulatory sequences, promoters, 5' and 3' untranslated regions and specific initiation signals (such as an ATG initiation codon and Kozak consensus sequence) which allow more efficient translation of sequences encoding the polypeptides of the present invention. In cases where the complete coding sequence, including the initiation codon and upstream //regulatory sequences, are inserted into the appropriate expression vector, additional control signals may not be needed. However, in cases where only coding sequence, or a fragment thereof, is inserted, exogenous translational control signals as described above should be provided by the vector. Such signals may be of various origins, both natural and synthetic. The efficiency of expression may be enhanced by the inclusion of enhancers appropriate for the particular host cell system used (Scharf et al., 1994).

The invention also includes nucleic acid molecules that are the complements of the sequences described herein.

According to still another aspect of the present invention there is provided an isolated DNA molecule comprising the nucleotide sequence set forth in any one of SEQ ID NOs: 1, 7-9, 11, 89-97, 108, 111-114, 136-144, and 153-154.

According to still another aspect of the present invention there is provided an isolated DNA molecule consisting of the nucleotide sequence set forth in any one of SEQ ID NOs: 1, 7-9, 11, 89-97, 108, 111-114, 136-144, and 153-154.

The present invention allows for the preparation of purified polypeptides or proteins from the polynucleotides of the present invention, or variants thereof. In order to do this, host cells may be transformed with a DNA molecule as described above. Typically said host cells are transfected with an expression vector comprising a DNA molecule according to the invention. A variety of expression vector/host systems may be utilized to contain and express sequences encoding polypeptides of the invention. These include, but are not limited to, microorganisms such as bacteria transformed with plasmid or cosmid DNA expression vectors; yeast transformed with yeast expression vectors; insect cell systems infected with viral expression vectors (e.g., baculovirus); or mouse or other animal or human tissue cell systems. Mammalian cells can be used to express a protein using various expression vectors including plasmid, cosmid and viral systems such as a vaccinia virus expression system. The invention is not limited by the host cell employed.

The polynucleotide sequences, or variants thereof, of the present invention can be stably expressed in cell lines to allow long term production of recombinant proteins in mammalian systems. Sequences encoding the polypeptides of the present invention can be transformed into cell lines using expression vectors which may contain viral origins of replication and/or endogenous expression elements and a selectable marker gene on the same or on a separate vector. The selectable marker confers resistance to a selective agent, and its presence allows growth and recovery of cells which successfully express the introduced sequences. Resistant clones of stably transformed cells may be propagated using tissue culture techniques appropriate to the cell type.

The protein produced by a transformed cell may be secreted or retained intracellularly depending on the sequence and/or the vector used. As will be understood by those of skill in the art, expression vectors containing polynucleotides which encode a protein may be designed to contain signal sequences which direct secretion of the protein through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, glycosylation, phosphorylation, and acylation. Post-translational cleavage of a "prepro" form of the protein may also be used to specify protein targeting, folding, and/or activity. Different host cells having specific cellular machinery and characteristic mechanisms for post-translational activities (e.g., CHO or HeLa cells), are available from the American Type Culture Collection (ATCC) and may be chosen to ensure the correct modification and processing of the foreign protein.

When large quantities of the gene are needed, such as for antibody production, vectors which direct high levels of expression of this protein may be used, such as those containing the T5 or T7 inducible bacteriophage promoter. The present invention also includes the use of the expression systems described above in generating and isolating fusion proteins which contain important functional domains of the protein. These fusion proteins are used for binding, structural and functional studies as well as for the generation of appropriate antibodies.

In order to express and purify the protein as a fusion protein, the appropriate polynucleotide sequences of the present invention are inserted into a vector which contains a nucleotide sequence encoding another peptide (for example, glutathionine succinyl transferase). The fusion protein is expressed and recovered from prokaryotic or eukaryotic cells. The fusion protein can then be purified by affinity chromatography based upon the fusion vector sequence. The desired protein is then obtained by enzymatic cleavage of the fusion protein.

Fragments of polypeptides of the present invention may also be produced by direct peptide synthesis using solid-phase techniques. Automated synthesis may be achieved by using the ABI 431A Peptide Synthesizer (Perkin-Elmer). Various fragments of this protein may be synthesized separately and then combined to produce the full length molecule.

According to still another aspect of the present invention there is provided an isolated polypeptide, said polypeptide being a mutant alpha subunit of a mammalian voltage-gated sodium channel, wherein a mutation event selected from the group consisting of point mutations, deletions, insertions and rearrangements has occurred and said mutation event disrupts the functioning of an assembled sodium channel so as to produce an epilepsy phenotype, with the proviso that said mutation event is not a T875M transition or a R1648H transition.

Preferably said mutation event occurs in an intracellular loop, preferably in the intracellular loop between transmembrane segments 2 and 3 in domain I, in the S4 segment of domain IV at amino acid position 1656, or in an S5 segment of a transmembrane domain of SCN1A. Preferably the mutation creates a phenotype of generalised epilepsy with febrile seizures plus.

In one form of the invention the mutation event is a substitution in which a highly conserved aspartic acid residue is replaced with a valine residue located in the intracellular domain located just outside the S3 segment of domain I of SCN1A. Preferably the substitution is a D188V transition as illustrated in SEQ ID NO.:2.

In a further form of the invention the mutation event is a substitution in which a highly conserved valine residue is replaced with a leucine residue located in the S5 segment of domain III of SCN1A. Preferably the substitution is a V1353L transition as illustrated in SEQ ID NO:4.

In a still further form of the invention the mutation event is a substitution in which a highly conserved isoleucine residue is replaced with a methionine residue located in the S4 segment of domain IV of SCN1A. Preferably the substitution is a I1656M transition as illustrated in SEQ ID NO:6.

In addition, the polymorphisms identified in Table 3 (SEQ ID Numbers:10 and 12) and Table 4 (SEQ ID NOs: 119-127 and 165-173) form part of the invention.

The isolated polypeptides of the present invention may have been subjected to one or more mutation events selected from the group consisting of substitutions, deletions, insertions and rearrangements in addition to the mutation associated with epilepsy. Typically these mutation events are conservative substitutions.

According to still another aspect of the present invention there is provided an isolated polypeptide comprising the sequence set forth in any one of SEQ ID NOs:2, 4, 6, 10, 12, 119-127 and 165-173.

According to still another aspect of the present invention there is provided a polypeptide consisting of the amino acid sequence set forth in any one of SEQ ID NOs:2, 4, 6, 10, 12, 119-127 and 165-173.

According to still another aspect of the present invention there is provided an isolated polypeptide complex, said polypeptide complex being an assembled mammalian voltage-gated sodium channel, wherein a mutation event selected from the group consisting of substitutions, deletions, insertions and rearrangements has occurred in the alpha subunit of the complex. Mutations include those in the intracellular loop between transmembrane segments 2 and 3, the S4 segment of domain IV at amino acid position 1656, or in an S5 segment of a transmembrane domain of the alpha subunit. In a particular aspect an assembled mammalian voltage-gated sodium channel bearing any such mutation in the alpha subunit will produce a phenotype of epilepsy, in particular generalised epilepsy with febrile seizures plus, or other disorders associated with sodium channel dysfunction including, but not restricted to, myotonias such as hyperkalaemic periodic paralysis, paramyotonia congenita and potassium aggravated myotonia, as well as cardiac arrhythmias such as long QT syndrome.

In a particular aspect there is provided a complex, being an assembled mammalian voltage-gated sodium channel, bearing a mutation in the intracellular loop between transmembrane segments 2 and 3, the S4 segment of domain IV at amino acid position 1656, or in an S5 segment of a transmembrane domain of the SCN1A subunit of the channel.

According to still another aspect of the present invention there is provided a method of preparing a polypeptide, said polypeptide being a mutant alpha subunit of a mammalian voltage-gated sodium channel, comprising the steps of:

(1) culturing host cells transfected with an expression vector comprising a DNA molecule as described above under conditions effective for polypeptide production; and (2) harvesting the mutant alpha subunit.

The mutant alpha subunit may also be allowed to assemble with other subunits of the sodium channel, whereby the assembled mutant sodium channel is harvested.

Substantially purified protein or fragments thereof can then be used in further biochemical analyses to establish secondary and tertiary structure for example by X-ray crystallography of crystals of the proteins or by nuclear magnetic resonance (NMR). Determination of structure allows for the rational design of pharmaceuticals to interact with the mutated sodium channel, alter the overall sodium channel protein charge configuration or charge interaction with other proteins, or to alter its function in the cell.

It will be appreciated that, having identified mutations involved in epilepsy in these proteins, the mutant sodium channel alpha subunits will be useful in further applications which include a variety of hybridisation and immunological assays to screen for and detect the presence of either a normal or mutated gene or gene product. The invention also enables therapeutic methods for the treatment of epilepsy and enables methods for the diagnosis of epilepsy. In particular the invention enables treatment and diagnosis of generalised epilepsy with febrile seizures plus, as well as other disorders associated with sodium channel dysfunction, as mentioned above.

Therapeutic Applications

According to one aspect of the invention there is provided a method of treating epilepsy, in particular generalised epilepsy with febrile seizures plus, as well as other disorders associated with sodium channel dysfunction, including but not restricted to, myotonias such as hyperkalaemic periodic paralysis, paramyotonia congenita and potassium aggravated myotonia, as well as cardiac arrhythmias such as long QT syndrome, comprising administering a selective agonist, antagonist or modulator of the sodium channel when a mutation event as described above has occurred, in particular, when it contains a mutation in the intracellular loop between transmembrane segments 2 and 3, in the S4 segment of domain IV at amino acid position 1656, or in an S5 segment of a transmembrane domain of an alpha subunit.

In still another aspect of the invention there is provided the use of a selective antagonist or modulator of the sodium channel when a mutation event as described above has occurred, in particular, to a sodium channel when it contains a mutation in the intracellular loop between transmembrane segments 2 and 3, in the S4 segment of domain IV at amino acid position 1656, or in an S5 segment of a transmembrane domain of an alpha subunit, said mutation being causative of a disorder including epilepsy, in particular generalised epilepsy with febrile seizures plus as well as other disorders associated with sodium channel dysfunction, including but not restricted to, myotonias such as hyperkalaemic periodic paralysis, paramyotonia congenita and potassium aggravated myotonia, as well as cardiac arrhythmias such as long QT syndrome, in the manufacture of a medicament for the treatment of the disorder.

In one aspect of the invention a suitable antagonist or modulator will restore wild-type function to the sodium channels that contain a mutation in an alpha subunit including those that form part of this invention.

Using methods well known in the art, a mutant sodium channel may be used to produce antibodies specific for the mutant channel that is causative of the disease or to screen libraries of pharmaceutical agents to identify those that specifically bind the mutant sodium channel.

In one aspect, an antibody, which specifically binds to a mutant sodium channel, may be used directly as an antagonist or modulator, or indirectly as a targeting or delivery mechanism for bringing a pharmaceutical agent to cells or tissues that express the mutant sodium channel.

In a still further aspect of the invention there is provided an antibody which is immunologically reactive with a polypeptide as described above, but not with a wild-type sodium channel or subunit thereof.

In particular, there is provided an antibody to an assembled sodium channel containing a mutation causative of a disorder as described above, in a subunit comprising the receptor. Such antibodies may include, but are not limited to, polyclonal, monoclonal, chimeric, and single chain antibodies as would be understood by the person skilled in the art.

For the production of antibodies, various hosts including rabbits, rats, goats, mice, humans, and others may be immunized by injection with a polypeptide as described or with any fragment or oligopeptide thereof which has immunogenic properties. Various adjuvants may be used to increase immunological response and include, but are not limited to, Freund's, mineral gels such as aluminum hydroxide, and surface-active substances such as lysolecithin. Adjuvants used in humans include BCG (bacilli Calmette-Guerin) and *Corynebacterium parvum*.

It is preferred that the oligopeptides, peptides, or fragments used to induce antibodies to the mutant sodium channel have an amino acid sequence consisting of at least 5 amino acids, and, more preferably, of at least 10 amino acids. It is also preferable that these oligopeptides, peptides, or fragments are identical to a portion of the amino acid sequence of the natural protein and contain the entire amino acid sequence of a small, naturally occurring molecule. Short stretches of sodium channel amino acids may be fused with those of another protein, such as KLH, and antibodies to the chimeric molecule may be produced.

Monoclonal antibodies to a mutant sodium channel may be prepared using any technique which provides for the production of antibody molecules by continuous cell lines in culture. These include, but are not limited to, the hybridoma technique, the human B-cell hybridoma technique, and the EBV-hybridoma technique. (For example, see Kohler et al., 1975; Kozbor et al., 1985; Cote et al., 1983; Cole et al., 1984).

Antibodies may also be produced by inducing in vivo production in the lymphocyte population or by screening immunoglobulin libraries or panels of highly specific binding reagents as disclosed in the literature. (For example, see Orlandi et al., 1989; Winter et al., 1991).

Antibody fragments which contain specific binding sites for a mutant sodium channel may also be generated. For example, such fragments include, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (For example, see Huse et al., 1989).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between a sodium channel and its specific antibody. A two-site, monoclonal-based immunoassay utilizing antibodies reactive to two non-interfering sodium channel epitopes is preferred, but a competitive binding assay may also be employed.

In a further aspect, a suitable agonist may include a small molecule that can restore wild-type activity of the sodium channel containing mutations in the alpha subunit as described above, or may include an antibody to a mutant sodium channel that is able to restore function to a normal level.

Small molecules suitable for therapeutic applications may be identified using nucleic acids and peptides of the invention in drug screening applications as described below.

In a further aspect of the invention there is provided a method of treating epilepsy, in particular generalised epilepsy with febrile seizures plus, as well as other disorders associated with sodium channel dysfunction, including but not restricted to, myotonias such as hyperkalaemic periodic paralysis, paramyotonia congenita and potassium aggravated myotonia, as well as cardiac arrhythmias such as long QT syndrome, comprising administering an isolated DNA molecule which is the complement (antisense) of any one of the DNA molecules described above and which encodes an RNA molecule that hybridizes with the mRNA encoding a mutant sodium channel alpha subunit, to a subject in need of such treatment.

Typically, a vector expressing the complement of the polynucleotides of the invention may be administered to a subject in need of such treatment. Antisense strategies may use a variety of approaches including the use of antisense oligonucleotides, injection of antisense RNA, ribozymes, DNAzymes and transfection of antisense RNA expression vectors. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (For example, see Goldman et al., 1997).

In a still further aspect of the invention there is provided the use of an isolated DNA molecule which is the complement of a DNA molecule of the invention and which encodes an RNA molecule that hybridizes with the mRNA encoding a mutant sodium channel alpha subunit, in the manufacture of a medicament for the treatment of epilepsy, in particular generalised epilepsy with febrile seizures plus, as well as other disorders associated with sodium channel dysfunction, including but not restricted to, myotonias such as hyperkalaemic periodic paralysis, paramyotonia congenita and potassium aggravated myotonia, as well as cardiac arrhythmias such as long QT syndrome.

In further embodiments, any of the agonists, antagonists, modulators, antibodies, complementary sequences or vectors of the invention may be administered alone or in combination with other appropriate therapeutic agents. Selection of the appropriate agents may be made by those skilled in the art, according to conventional pharmaceutical principles. The combination of therapeutic agents may act synergistically to effect the treatment or prevention of the various disorders described above. Using this approach, therapeutic efficacy with lower dosages of each agent may be possible, thus reducing the potential for adverse side effects.

Drug Screening

According to still another aspect of the invention, peptides of the invention, particularly purified mutant sodium channel alpha subunit polypeptide and cells expressing these, are useful for the screening of candidate pharmaceutical agents in a variety of techniques. It will be appreciated that therapeutic agents useful in the treatment of epilepsy, in particular generalised epilepsy with febrile seizures plus, as well as other disorders associated with sodium channel dysfunction, including but not restricted to, myotonias such as hyperkalaemic periodic paralysis, paramyotonia congenita and potassium aggravated myotonia, as well as cardiac arrhythmias such as long QT syndrome, are likely to show binding affinity to the polypeptides of the invention.

Such techniques include, but are not limited to, utilising eukaryotic or prokaryotic host cells that are stably transformed with recombinant molecules expressing the polypeptide or fragment, preferably in competitive binding assays. Binding assays will measure for the formation of complexes between a mutated sodium channel alpha subunit polypeptide or fragment and the agent being tested, or will measure the degree to which an agent being tested will interfere with the formation of a complex between a mutated sodium channel alpha subunit polypeptide or fragment and a known ligand.

Another technique for drug screening provides highthroughput screening for compounds having suitable binding affinity to the mutant sodium channel alpha subunit polypeptides or sodium channels containing these (see PCT published application WO84/03564). In this stated technique, large numbers of small peptide test compounds can be synthesised on a solid substrate and can be assayed through mutant sodium channel or mutant sodium channel alpha subunit polypeptide binding and washing. Bound mutant sodium channel or mutant sodium channel alpha subunit polypeptide is then detected by methods well known in the art. In a variation of this technique, purified polypeptides of the invention can be coated directly onto plates to identify interacting test compounds.

The invention also contemplates the use of competition drug screening assays in which neutralizing antibodies capable of specifically binding the mutant sodium channel compete with a test compound for binding thereto. In this manner, the antibodies can be used to detect the presence of any peptide that shares one or more antigenic determinants of the mutant sodium channel.

The invention is particularly useful for screening compounds by using the polypeptides of the invention in transformed cells, transfected or injected oocytes, or transgenic animals. A particular drug is added to the cells in culture or administered to a transgenic animal containing the mutant sodium channel and the effect on the current of the channel is compared to the current of a cell or animal containing the wild-type sodium channel. Drug candidates that alter the current to a more normal level are useful for treating or preventing epilepsy, in particular generalised epilepsy with febrile seizures plus as well as other disorders associated with sodium channel dysfunction, as described above.

The polypeptides of the present invention may also be used for screening compounds developed as a result of combinatorial library technology. This provides a way to test a large number of different substances for their ability to modulate activity of a polypeptide. The use of peptide libraries is preferred (see WO 97/02048) with such libraries and their use known in the art.

A substance identified as a modulator of polypeptide function may be peptide or non-peptide in nature. Non-peptide "small molecules" are often preferred for many in vivo pharmaceutical applications. In addition, a mimic or mimetic of the substance may be designed for pharmaceutical use. The design of mimetics based on a known pharmaceutically active compound ("lead" compound) is a common approach to the development of novel pharmaceuticals. This is often desirable where the original active compound is difficult or expensive to synthesise or where it provides an unsuitable method of administration. In the design of a mimetic, particular parts of the original active compound that are important in determining the target property are identified. These parts or residues constituting the active region of the compound are known as its pharmacophore. Once found, the pharmacophore structure is modelled according to its physical properties using data from a range of sources including x-ray diffraction data and NMR. A template molecule is then selected onto which chemical groups which mimic the pharmacophore can be added. The selection can be made such that the mimetic is easy to synthesise, is likely to be pharmacologically acceptable, does not degrade in vivo and retains the biological activity of the lead compound. Further optimisation or modification can be carried out to select one or more final mimetics useful for in vivo or clinical testing.

It is also possible to isolate a target-specific antibody and then solve its crystal structure. In principle, this approach yields a pharmacophore upon which subsequent drug design can be based as described above. It may be possible to avoid protein crystallography altogether by generating anti-idiotypic antibodies (anti-ids) to a functional, pharmacologically active antibody. As a mirror image of a mirror image, the binding site of the anti-ids would be expected to be an analogue of the original receptor. The anti-id could then be used to isolate peptides from chemically or biologically produced peptide banks.

Any of the therapeutic methods described above may be applied to any subject in need of such therapy, including, for example, mammals such as dogs, cats, cows, horses, rabbits, monkeys, and most preferably, humans.

Diagnostic Applications

Polynucleotide sequences of the invention may be used for the diagnosis of epilepsy, in particular generalised epilepsy with febrile seizures plus, as well as other disorders associated with sodium channel dysfunction, including but not restricted to, myotonias such as hyperkalaemic periodic paralysis, paramyotonia congenita and potassium aggravated myotonia, as well as cardiac arrhythmias such as long QT syndrome, and the use of the DNA molecules of the invention in diagnosis of these disorders, is therefore contemplated.

In another embodiment of the invention, the polynucleotides that may be used for diagnostic purposes include oligonucleotide sequences, genomic DNA and complementary RNA and DNA molecules. The polynucleotides may be used to detect and quantitate gene expression in biological samples. Genomic DNA used for the diagnosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, hybridisation using specific oligonucleotides, restriction enzyme digest and mapping, PCR mapping, RNAse protection, and various other methods may be employed. For instance direct nucleotide sequencing of amplification products from the GABA receptor subunits can be employed. Sequence of the sample amplicon is compared to that of the wild-type amplicon to determine the presence (or absence) of nucleotide differences.

According to a further aspect of the invention there is provided the use of a polypeptide as described above in the diagnosis of epilepsy, in particular generalised epilepsy with febrile seizures plus, as well as other disorders associated with sodium channel dysfunction, as described above.

When a diagnostic assay is to be based upon mutant proteins constituting a sodium channel, a variety of approaches are possible. For example, diagnosis can be achieved by monitoring differences in the electrophoretic mobility of normal and mutant alpha subunit proteins that form part of the sodium channel. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In another aspect, antibodies that specifically bind mutant sodium channels may be used for the diagnosis of epilepsy, or in assays to monitor patients being treated with agonists, antagonists, modulators or inhibitors of the mutant sodium channel. Antibodies useful for diagnostic purposes may be prepared in the same manner as described above for therapeutics. Diagnostic assays to detect mutant sodium channels include methods that utilize the antibody and a label to detect a mutant sodium channel in human body fluids or in extracts of cells or tissues. The antibodies may be used with or without modification, and may be labelled by covalent or non-covalent attachment of a reporter molecule.

A variety of protocols for measuring the presence of mutant sodium channels, including ELISAs, RIAs, and FACS, are known in the art and provide a basis for diagnosing epilepsy, in particular generalised epilepsy with febrile seizures plus, as well as other disorders associated with sodium channel dysfunction, as described above. The expression of a mutant channel is established by combining body fluids or cell extracts taken from test mammalian subjects, preferably human, with antibody to the channel under conditions suitable for complex formation. The amount of complex formation may be quantitated by various methods, preferably by photometric means. Antibodies specific for the mutant channel will only bind to individuals expressing the said mutant channel and not to individuals expressing only wild-type channels (ie normal individuals). This establishes the basis for diagnosing the disease.

Once an individual has been diagnosed with the disorder, effective treatments can be initiated. These may include administering a selective modulator of the mutant channel or an antagonist to the mutant channel such as an antibody or mutant complement as described above. Alternative treatments include the administering of a selective agonist or modulator to the mutant channel so as to restore channel function to a normal level.

Microarray

In further embodiments, complete cDNAs, oligonucleotides or longer fragments derived from any of the polynucleotide sequences described herein may be used as probes in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents. Microarrays may be prepared, used, and analyzed using methods known in the art. (For example, see Schena et al., 1996; Heller et al., 1997).

According to a further aspect of the present invention, neurological material obtained from animal models generated as a result of the identification of specific sodium channel alpha subunit human mutations, particularly those disclosed in the present invention, can be used in microarray experiments. These experiments can be conducted to identify the level of expression of specific sodium channel alpha subunits, or any cDNA clones from whole-brain libraries, in epileptic brain tissue as opposed to normal control brain tissue. Variations in the expression level of genes, including sodium channel alpha subunits, between the two tissues indicates their involvement in the epileptic process either as a cause or consequence of the original sodium channel mutation present in the animal model. Microarrays may be prepared, as described above.

Transformed Hosts

The present invention also provides for the production of genetically modified (knock-out, knock-in and transgenic), non-human animal models transformed with the DNA molecules of the invention. These animals are useful for the study of the function of a sodium channel, to study the mechanisms of disease as related to a sodium channel, for the screening of candidate pharmaceutical compounds, for the creation of explanted mammalian cell cultures which express a mutant sodium channel and for the evaluation of potential therapeutic interventions.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, genetically modified mice and rats are highly desirable due to their relative ease of maintenance and shorter life spans. For certain studies, transgenic yeast or invertebrates may be suitable and preferred because they allow for rapid screening and provide for much easier handling. For longer term studies, non-human primates may be desired due to their similarity with humans.

To create an animal model for a mutated sodium channel several methods can be employed. These include but are not limited to generation of a specific mutation in a homologous animal gene, insertion of a wild type human gene and/or a humanized animal gene by homologous recombination, insertion of a mutant (single or multiple) human gene as genomic or minigene cDNA constructs using wild type or mutant or artificial promoter elements or insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To create a transgenic mouse, which is preferred, a mutant version of a sodium channel alpha subunit can be inserted into a mouse germ line using standard techniques of oocyte microinjection or transfection or microinjection into embryonic stem cells. Alternatively, if it is desired to inactivate or replace an endogenous sodium channel alpha subunit gene, homologous recombination using embryonic stem cells may be applied.

For oocyte injection, one or more copies of the mutant sodium channel alpha subunit gene can be inserted into the pronucleus of a just-fertilized mouse oocyte. This oocyte is then reimplanted into a pseudo-pregnant foster mother. The liveborn mice can then be screened for integrants using analysis of tail DNA or DNA from other tissues for the presence of the particular human subunit gene sequence. The transgene can be either a complete genomic sequence injected as a YAC, BAC, PAC or other chromosome DNA fragment, a complete cDNA with either the natural promoter or a heterologous promoter, or a minigene containing all of the coding region and other elements found to be necessary for optimum expression.

According to still another aspect of the invention there is provided the use of genetically modified non-human animals as described above for the screening of candidate pharmaceutical compounds.

It will be clearly understood that, although a number of prior art publications are referred to herein, this reference does not constitute an admission that any of these documents forms part of the common general knowledge in the art, in Australia or in any other country.

Throughout this specification and the claims, the words "comprise", "comprises" and "comprising" are used in a non-exclusive sense, except where the context requires otherwise.

BRIEF DESCRIPTION OF THE DRAWINGS

Preferred forms of the invention are described, by way of example only, with reference to the following examples and the accompanying drawings, in which:

FIG. 1. Generalised epilepsy with febrile seizures plus (GEFS+) pedigrees are shown for the three families. DNA was not available from those individuals not assigned a letter (X, Y, or Z) or a 0. A: Pedigree of an Australian family with individual numbering for this family based on FIG. 1 in Scheffer & Berkovic (1997). B: Pedigree of an Ashkenazi family. C: Pedigree of a Druze family.

FIG. 3. Sodium channel amino acid alignments. Alignment of sodium channel amino acids surrounding the three SCN1A mutations.

FIG. 1D: Autosomal dominant disorders can be attributed to single ion channel subunit mutations that give rise to severe functional consequences.

FIG. 6 provides examples of epilepsy pedigrees where mutation profiles of ion channel subunits for individuals constituting the pedigree have begun to be determined. These examples have been used to illustrate how the identification of novel ion channel subunit mutations and variations in IGE individuals can combine to give rise to the disorder.

MODES FOR PERFORMING THE INVENTION

EXAMPLE 1

Clinical Diagnosis of Affected Family Members

A group of 53 unrelated probands with GEFS+ phenotypes were studied. These subjects were ascertained on the basis of twin and family studies and on the basis of routine clinical practice. Phenotypes in probands and family members were classified as described elsewhere (Scheffer & Berkovic 1997; Singh et al 1999). Familial cases (n=36) were those in which at least one first-degree relative of the proband had a phenotype within the GEFS+ spectrum. Informed consent was obtained from all subjects.

Figure 1A:
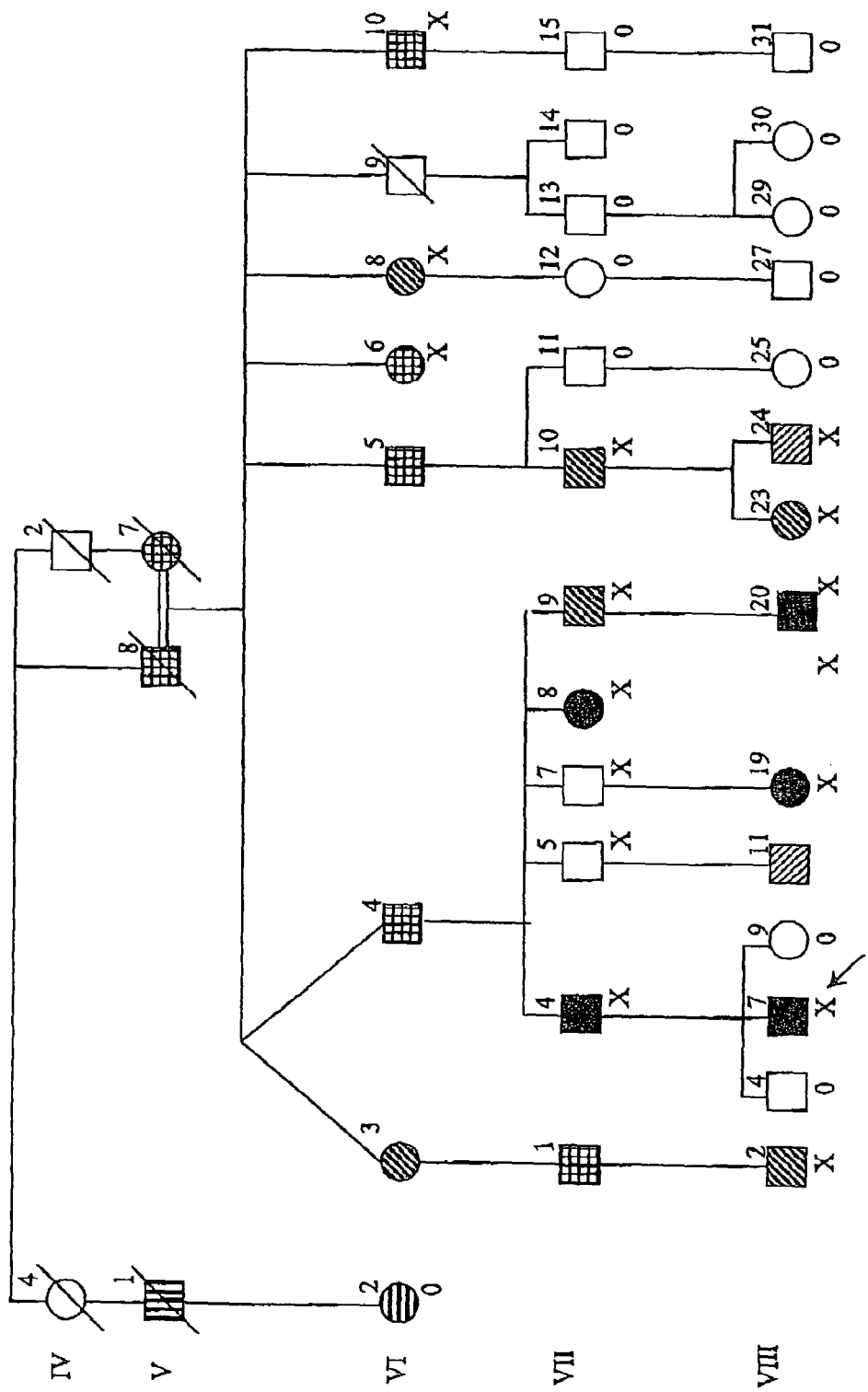
FIG. 1A: A typical channel may have five subunits of three different types.

The Australian family in FIG. 1A, which has been described extensively elsewhere (Scheffer & Berkovic, 1997; Lopes-Cendes et al, 2000), is the original pedigree leading to the initial delineation and description of the GEFS+ syndrome.

Figure 1B:
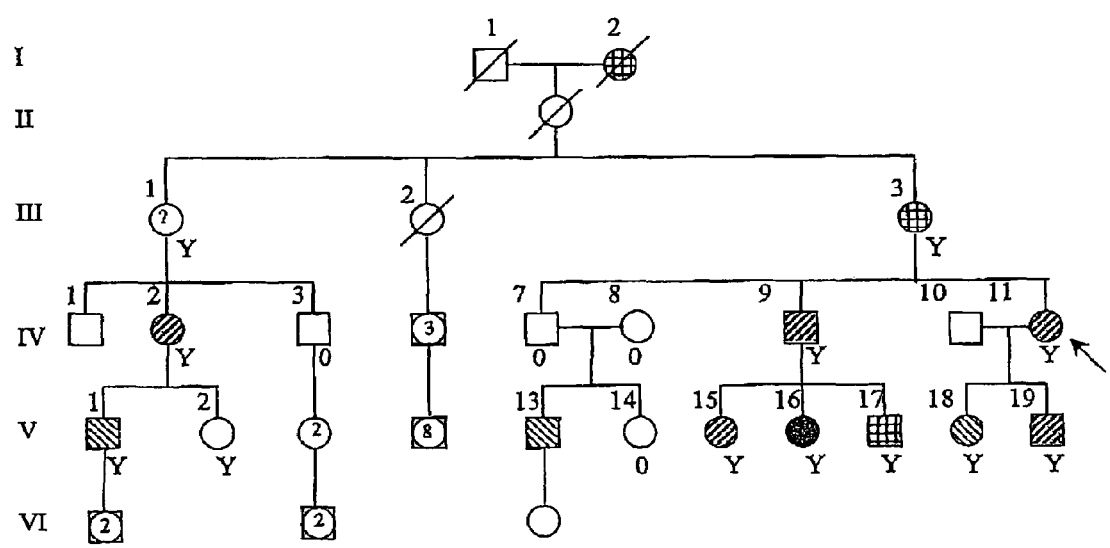
FIG. 1B: In outbred populations complex diseases such as idiopathic generalized epilepsies may be due to mutations in two (or more) different subunit genes. Because only one allele of each subunit gene is abnormal, half the expressed subunits will have the mutation.

The Israeli family in FIG. 1B is of Ashkenazi origin and spans six generations. Twelve family members had seizures. In the two oldest members (I-2, III-3) seizures had occurred in childhood but the data were insufficient to allow classification of the phenotype. Of the 10 other family members who had seizures, 3 had febrile seizures with onset at age 9-13 months. All attacks occurred with fever and offset occurred between 1 and 4 years with 1 to 7 attacks each. Five had febrile seizures plus with onset at age 9-24 months, offset between 5 and 41 years and 2 to 15 attacks each. Seizures during childhood were a mixture of febrile seizures and afebrile tonic-clonic seizures, whereas the rarely occurring seizures during teenage and adult years were all afebrile. Subject V-16 had a more severe phenotype with approximately 20 febrile seizures at age 6 months to 5 years, 10 afebrile tonic-clonic seizures at age 5 to 15 years and occasional complex partial seizures associated with mild learning difficulties. She was classified as having febrile seizures plus and complex partial seizures. Her older sister (V-15) had typical febrile seizures plus, but their younger brother (V-17), aged 14 years, had no febrile seizures but had two afebrile tonic-clonic seizures at ages 12 years 6 months and 14 years. For purposes of linkage analysis, he was regarded as affected, although he had only afebrile tonic-clonic seizures. All affected subjects were of normal or superior intellect, except V-16 (see above) and all had a normal neurological examination. Electroencephalography (EEG) studies had been performed infrequently during the active phase of the epilepsy, and the results usually either were normal or were reported to show generalised discharges.

Figure 1C:
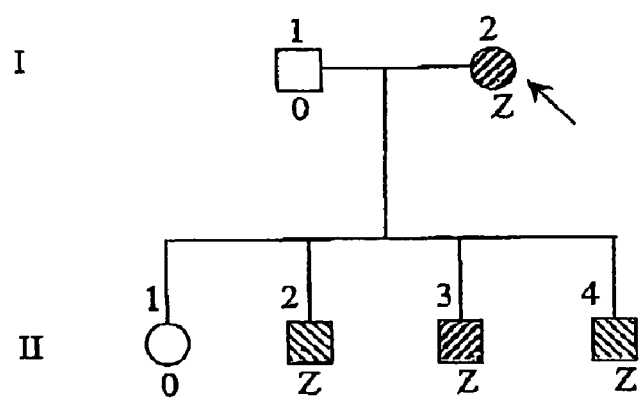
FIG. 1C: In inbred populations, both alleles of a single subunit gene will be affected, so all expressed subunits will be mutated.

The second Israeli family was of Druze origin; the parents were from different but proximate villages and were not known to be related. This family spans two generations, and four family members had seizures (FIG. 1C). The proband aged 41 years (I-2) had had hundreds of tonic-clonic seizures, sometimes with fever. These began at age 4 years and continued, at a rate of approximately one per month, until the time of the study. The proband was mildly intellectually impaired. EEG showed generalized irregular spike-wave and polyspike-wave discharges, and febrile seizures plus was diagnosed. Of her four children, the oldest was unaffected (II-1), two had febrile seizures (II-2, II-4) and one had febrile seizures plus (II-3).

EXAMPLE 2

Isolation and Sequencing of SCN1A Genomic Clones

At the commencement of this study the full-length sequence of the human SCN1A gene was not known. To determine this sequence a human BAC library obtained from Genome Systems was initially screened to identify human genomic sequence clones containing the SCN1A gene. The BAC filters were screened with a PCR product amplified with the primer pair 5' AGATGACCAGAGTGAATATGTGAC-TAC 3' (SEQ ID NO:13) and 5' CCAATGG-TAAAATAATAATGGCGT 3' (SEQ ID NO:14) designed from the partial cDNA sequence of human SCN1A (Genbank Accession Number X65362).

The BAC filters were hybridised and washed according to manufacturers recommendations. Initially, membranes were individually pre-hybridised in large glass bottles for at least 2 hours in 20 ml of 6×SSC; 0.5% SDS; 5× Denhardt's; 100 ug/ml denatured salmon sperm DNA at 65° C. Overnight hybridisations with [$\alpha$-$^{32}$P]dCTP labelled probes were performed at 65° C. in 20 ml of a solution containing 6×SSC; 0.5% SDS; 100 ug/ml denatured salmon sperm DNA. Filters were washed sequentially in solutions of 2×SSC; 0.5% SDS (room temperature 5 minutes), 2×SSC; 0.1% SDS (room temperature 15 minutes) and 0.1×SSC; 0.5% SDS (37° C. 1 hour if needed).

A number of BAC clones were identified from this hybridisation and BAC129e04 was selected for subcloning and sequencing. DNA from this BAC clone was sheared by nebulisation (10 psi for 45 seconds). Sheared DNA was then blunt ended using standard methodologies (Sambrook et al., 1989) and run on an agarose gel in order to isolate DNA in the 2-4 Kb size range. These fragments were cleaned from the agarose using QIAquick columns (Qiagen), ligated into puc18 and used to transform competent XL-1 Blue E. coli cells. DNA was isolated from transformed clones and was sequenced using vector specific primers on an ABI377 sequencer to generate 1× coverage of the BAC clone. Sequence data were assembled in contigs using the Phred, Phrap and Gap4 high throughput sequencing software. Exon-intron boundaries were predicted based on the rat Scn1a cDNA sequence (Genbank Accession Number M22253) due to the full length human cDNA sequence of SCN1A not being known.

The human SCN1A gene was determined to be 8,381 base pair in length and is organised into 27 exons spanning over 100 Kb of genomic DNA. To facilitate a comparison with related sodium channels SCN4A, SCN5A and SCN8A, the first untranslated exon of SCN1A is designated exon 1A and the second exon, containing the start codon, remains exon 1 (Table 1). The SCN1A gene shows high homology to SCN2A and SCN3A at both the DNA and protein level. The close proximity of these genes to each other on chromosome 2 indicates likely duplication events during the evolution of the sodium channel gene family. Compared to SCN4A and SCN8A, additional sequence is present in the 3'UTR of SCN1A, giving the final exon an overall length of ~3.3 Kb.

Inspection of the splice junctions of SCN1A shows that there is close agreement with consensus splice motifs, with all introns bounded by GT-AG, except for two (introns 2 and 23). These introns exhibit deviation from the consensus splice pattern and are bounded by AT-AC terminal dinucleotides. These rare splice site variations are conserved in other characterised sodium channel subunits (SCN4A, SCN8A and the more distantly related SCN5A), indicating their ancient origin.

The intron positions are also highly conserved between sodium channel subunits, with most variation seen in the region that codes for the cytoplasmic loop between domains I and II of the gene (Table 1). Within this region, alternative splicing of exon 11 of SCN1A was found that was comparable to the alternative splicing of exon 10B in SCN8A (Plummer et al. 1998). Cytoplasmic loop 1 varies in both length and composition and is the proposed site of functional diversity among different sodium channels (Plummer & Meisler, 1999).

EXAMPLE 3

Analysis of SCN1A for Mutations in Epilepsy

The determination of the genomic structure of SCN1A allowed the design of intronic primers (Table 2 and SEQ ID Numbers: 15-88) to amplify each of the 27 exons of SCN1A in order to test for mutations in patients with generalised epilepsy with febrile seizures plus (GEFS+). A total of 53 unrelated patients (as described above) were screened by fluorescent single stranded conformation polymorphism (SSCP) analysis.

HEX-labelled primers were designed to amplify all exons of SCN1A (Table 2). A 30 ng sample of patient DNA was amplified in a total volume of 10 ul. Products were separated on non-denaturing 4% polyacrylamide gels containing 2% glycerol using the GelScan 2000 (Corbett Research). PCR products showing a conformational change were reamplified from 100 ng of genomic DNA with unlabelled primers and sequenced using the BigDye Terminator ready reaction kit (Perkin Elmer) according to manufacturers instructions.

Figure 2:
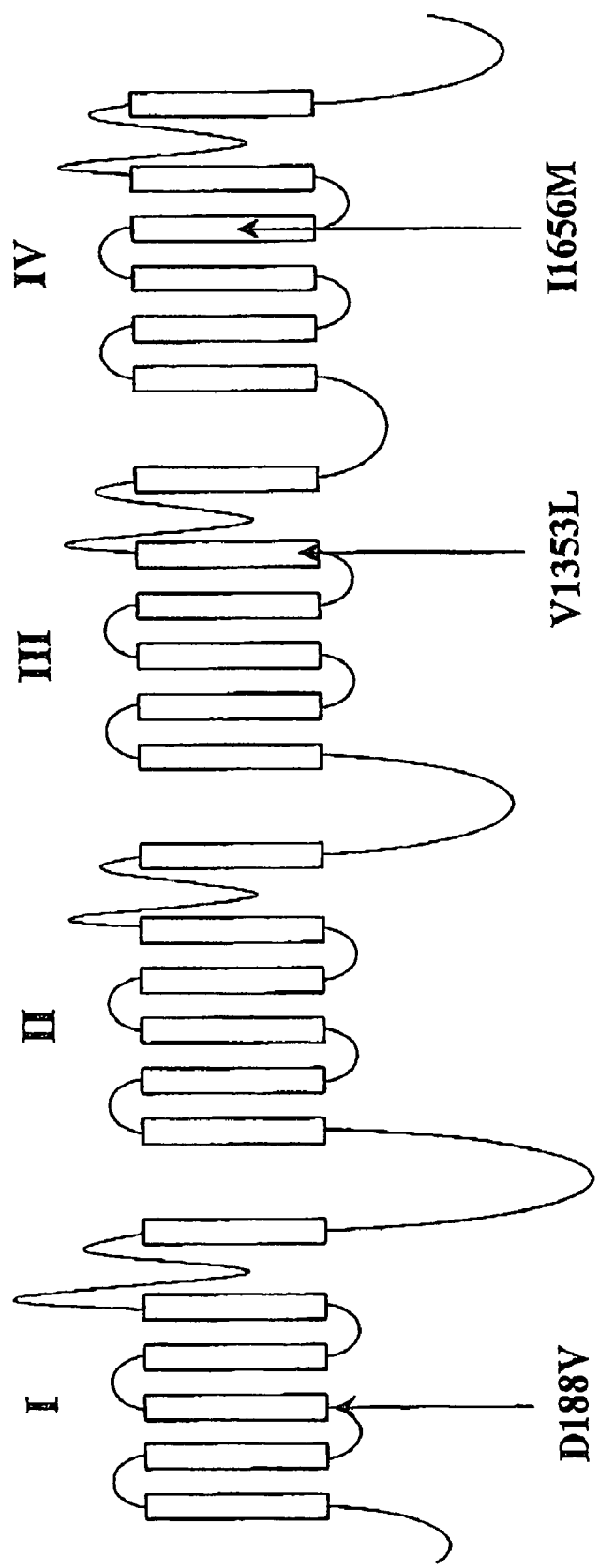
FIG. 2. Schematic of the alpha subunit of the sodium channel (SCN1A), showing the position of the three mutations identified in this study.
Figure 4:
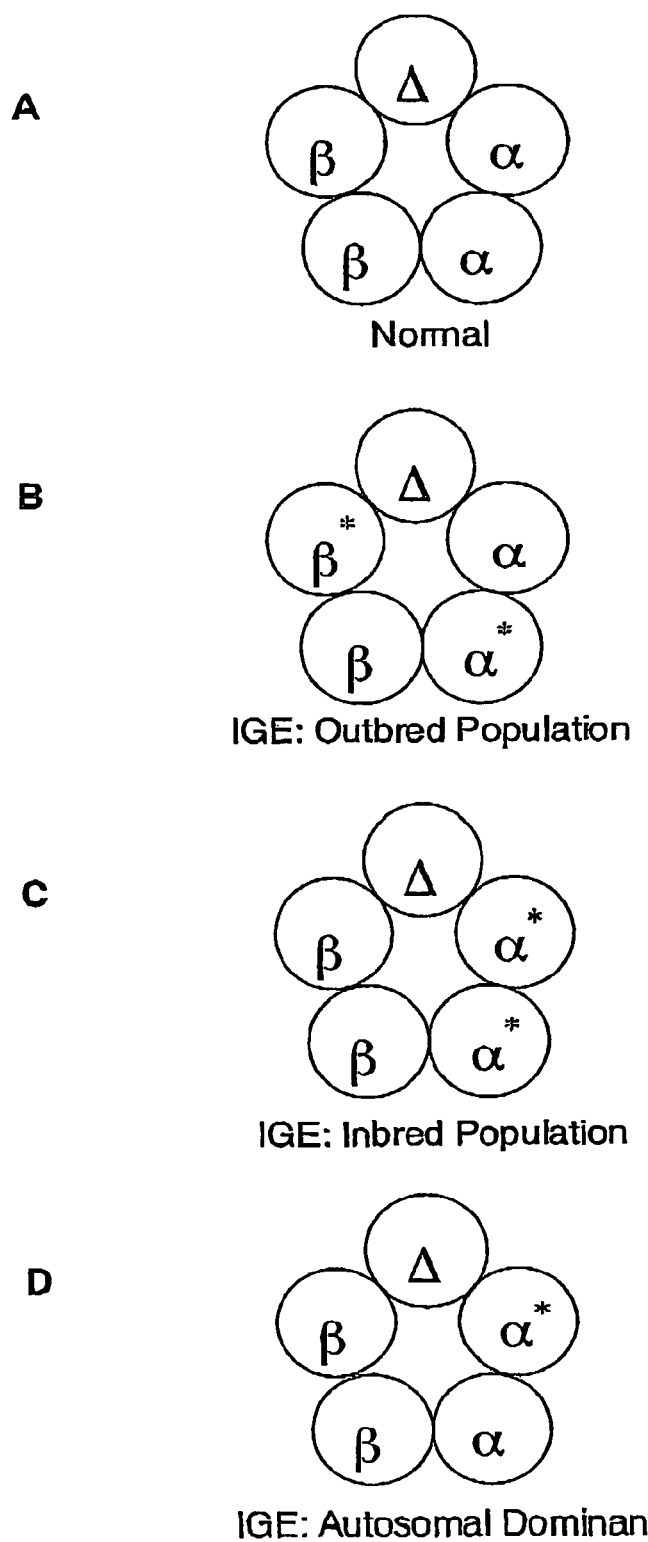
FIG. 4 provides an example of ion channel subunit stoichiometry and the effect of multiple versus single ion channel subunit mutations.

A total of 53 unrelated patients with GEFS+ were screened by fluorescent SSCP, including two families consistent with mapping to the same location as SCN1A on chromosome 2 (FIGS. 1A and 1B). No mutations were found in 17 sporadic cases of GEFS+ that were tested. Of the 36 families tested, 3 were found to have point mutations in SCN1A, which alter the amino acid sequence and are not present in the control population (n=60). The phenotype in the family in FIG. 1A previously had been mapped to chromosome 2 (Lopes-Cendes et al. 2000) and carries an A to T mutation at position 563 of the SCN1A coding sequence. This mutation segregates with affected family members. This mutation in exon 4 of SCN1A results in a D188V amino acid substitution that lies just outside the S3 segment of domain I (FIG. 2). The aspartic acid residue is conserved in all identified sodium channels in humans as well as in many different animal species, except the jellyfish which has an arginine at this residue and the flatworm which has a serine (FIG. 3). The published rat Scn2a sequence (Genbank Accession Number NM_012647) also has an arginine in place of the aspartic acid at residue 188.

A mutation in exon 21 (G to C nucleotide change at position 4057 of the SCN1A coding sequence) was found to segregate with GEFS+ in the Ashkenazi family (FIG. 1B). This mutation changes a highly conserved amino acid (V1353L) located in the S5 segment of domain III (FIG. 2). One family member (V-13) did not carry the mutation (FIG. 1B). This was determined by testing the DNA of a parent of this family member, since the subjects DNA was unavailable. This individual, who had typical febrile seizures that terminated at an early age, is likely to be a phenocopy. Mutations in the S5 segment of SCN4A that cause hyperkalemic periodic paralysis have been shown also to affect the rate of channel inactivation (Bendahhou et al., 1999)

A third mutation (C to G nucleotide change at position 4968 of the SCN1A coding sequence) discovered in the Druze family (FIG. 1C), changes an amino acid (I1656M) in the S4 segment of domain IV (FIG. 2). The S4 segment has a role in channel gating and mutations in this region of SCN1A reduce the rate of inactivation (Kuhn and Greef, 1996).

During the mutation screen of SCN1A several single nucleotide polymorphisms (SNPs) were identified (Table 3). The R1928G variant was found at low frequency in both GEFS+ and control populations. The T1067A variant was common in both populations and the remaining SNPs identified did not alter the amino acid sequence of SCN1A (Table 3).

EXAMPLE 4

Analysis of a Mutated Sodium Channels and Sodium Channel Alpha Subunits

The following methods are used to determine the structure and function of mutated sodium channel or sodium channel alpha subunits.

Molecular Biological Studies

The ability of the mutated sodium channel as a whole or through individual alpha subunits to bind known and unknown proteins can be examined. Procedures such as the yeast two-hybrid system are used to discover and identify any functional partners. The principle behind the yeast two-hybrid procedure is that many eukaryotic transcriptional activators, including those in yeast, consist of two discrete modular domains. The first is a DNA-binding domain that binds to a specific promoter sequence and the second is an activation domain that directs the RNA polymerase II complex to transcribe the gene downstream of the DNA binding site. Both domains are required for transcriptional activation as neither domain can activate transcription on its own. In the yeast two-hybrid procedure, the gene of interest or parts thereof (BAIT), is cloned in such a way that it is expressed as a fusion to a peptide that has a DNA binding domain. A second gene, or number of genes, such as those from a cDNA library (TARGET), is cloned so that it is expressed as a fusion to an activation domain. Interaction of the protein of interest with its binding partner brings the DNA-binding peptide together with the activation domain and initiates transcription of the reporter genes. The first reporter gene will select for yeast cells that contain interacting proteins (this reporter is usually a nutritional gene required for growth on selective media) The second reporter is used for confirmation and while being expressed in response to interacting proteins it is usually not required for growth.

The nature of the genes and proteins interacting with the mutant sodium channels can also be studied such that these partners can also be targets for drug discovery.

Structural Studies

Recombinant proteins corresponding to mutated sodium channel alpha subunits can be produced in bacterial, yeast, insect and/or mammalian cells and used in crystallographical and NMR studies. Together with molecular modeling of the protein, structure-driven drug design can be facilitated.

EXAMPLE 5

Generation of Polyclonal Antibodies Against a Mutant Sodium Channel or Sodium Channel Alpha Subunit Following the identification of new mutations in the alpha subunit of the sodium channel in individuals with generalised epilepsy with febrile seizures plus, antibodies can be made to the mutant channel which can selectively bind and distinguish mutant from normal protein. Antibodies specific for mutagenised epitopes are especially useful in cell culture assays to screen for cells which have been treated with pharmaceutical agents to evaluate the therapeutic potential of the agent.

To prepare polyclonal antibodies, short peptides can be designed homologous to a sodium channel subunit amino acid sequence. Such peptides are typically 10 to 15 amino acids in length. These peptides should be designed in regions of least homology to other receptor subunits and should also have poor homology to the mouse orthologue to avoid cross species interactions in further down-stream experiments such as monoclonal antibody production. Synthetic peptides can then be conjugated to biotin (Sulfo-NHS-LC Biotin) using standard protocols supplied with commercially available kits such as the PIERCE™ kit (PIERCE). Biotinylated peptides are subsequently complexed with avidin in solution and for each peptide complex, 2 rabbits are immunized with 4 doses of antigen (200 ug per dose) in intervals of three weeks between doses. The initial dose is mixed with Freund's Complete adjuvant while subsequent doses are combined with Freund's Immuno-adjuvant. After completion of the immunization, rabbits are test bled and reactivity of sera is assayed by dot blot with serial dilutions of the original peptides. If rabbits show significant reactivity compared with pre-immune sera, they are then sacrificed and the blood collected such that immune sera can be separated for further experiments.

This procedure is repeated to generate antibodies against wild-type forms of receptor subunits. The antibodies specific for mutant sodium channels can subsequently be used to detect the presence and the relative level of the mutant forms in various tissues.

EXAMPLE 6

Generation of monoclonal Antibodies Against a Mutant Sodium Channel or Sodium Channel Alpha Subunit Monoclonal antibodies can be prepared in the following manner. Immunogen, comprising intact mutated sodium channel or sodium channel alpha subunit peptides, is injected in Freund's adjuvant into mice with each mouse receiving four injections of 10 ug to 100 ug of immunogen. After the fourth injection blood samples taken from the mice are examined for the presence of antibody to the immunogen. Immune mice are sacrificed, their spleens removed and single cell suspensions are prepared (Harlow and Lane, 1988). The spleen cells serve as a source of lymphocytes, which are then fused with a permanently growing myeloma partner cell (Kohler and Milstein, 1975). Cells are plated at a density of 2×10⁵ cells/well in 96 well plates and individual wells are examined for growth. These wells are then tested for the presence of sodium channel specific antibodies by ELISA or RIA using wild type or mutant subunit target protein. Cells in positive wells are expanded and subcloned to establish and confirm monoclonality. Clones with the desired specificity are expanded and grown as ascites in mice followed by purification using affinity chromatography using Protein A Sepharose, ion-exchange chromatography or variations and combinations of these techniques.

TABLE 1

Comparison of Exon Sizes of SCN1A with Other Human SCNA Subunits

| SCN1A | | SCN4A | | SCN8A | | SCN5A | | |
|---|---|---|---|---|---|---|---|---|
| Exon No. | Exon Size | Exon No. | Exon Size | Exon No. | Exon Size | Exon No. | Exon Size | |
| 1A | 217 | – | – | – | – | 1 | 98 | |
| 1 | 313 | 1 | 661 | 1 | 276 | 2 | 324 | |
| 2 | 119 | 2 | 119 | 2 | 121 | 3 | 119 | |
| 3 | 90 | 3 | 90 | 3 | 88 | 4 | 90 | |
| 4 | 129 | 4 | 129 | 4 | 129 | 5 | 129 | |
| 5 | 92 | 5 | 92 | 5 | 92 | 6 | 92 | |
| 6 | 270 | 6 | 333 | 6 | 222 | 7 | 231 | |
| 7 | 64 | 7 | 64 | 7 | 64 | 8 | 64 | D I |
| 8 | 142 | 8 | 142 | 8 | 142 | 9 | 142 | |
| 9 | 207 | 9 | 210 | 9 | 207 | 10 | 198 | |
| 10 | 285 | 10 | 154 | 10A | 294 | 11 | 180 | |
| 11 | 381 | – | – | 10B | 396 | 12 | 372 | |
| 12 | 133 | – | – | 10C | 133 | 13 | 133 | |
| 13 | 239 | 11 | 239 | 11 | 239 | 14 | 239 | C loop 1 |
| 14 | 174 | 12 | 174 | 12 | 174 | 15 | 174 | |
| 15 | 357 | 13 | 357 | 13 | 357 | 16 | 351 | |
| 16 | 493 | 14 | 477 | 14 | 471 | 17 | 441 | |
| | | | | | | 18 | 162 | D II |
| 17 | 121 | 15 | 136 | 15 | 118 | 19 | 121 | |
| 18 | 155 | 16 | 155 | 16 | 155 | 20 | 155 | |
| 19 | 174 | 17 | 174 | 17 | 174 | 21 | 174 | C loop 2 |
| 20 | 123 | 18 | 123 | 18A | 123 | 22 | 123 | |
| 21 | 282 | 19 | 279 | 19 | 285 | 23 | 282 | |
| 22 | 54 | 20 | 54 | 20 | 54 | 24 | 54 | |
| 23 | 138 | 21 | 138 | 21 | 138 | 25 | 138 | D III |
| 24 | 105 | 22 | 105 | 22 | 105 | 26 | 105 | |
| 25 | 271 | 23 | 271 | 23 | 271 | 27 | 271 | |
| 26 | 2363 | 24 | >2242 | 24 | >1158 | 28 | 3257 | |
| | | | | | | | | D IV |

Note:
D: Transmembrane domain; C: Cytoplasmic loop.

TABLE 2

Primer Sequences Used for Mutation Analysis of SCN1A

| Exon | Forward Primer | Reverse Primer | Size (bp) |
|---|---|---|---|
| 1A | TACCATAGAGTGAGGCGAGG | ATGGACTTCCTGCTCTGCCC | 356 |
| 1 | CCTCTAGCTCATGTTTCATGAC | TGCAGTAGGCAATTAGCAGC | 448 |
| 2 | CTAATTAAGAAGAGATCCAGTGACAG | GCTATAAAGTGCTTACAGATCATGTAC | 356 |
| 3 | CCCTGAATTTTGGCTAAGCTGCAG | CTACATTAAGACACAGTTTCAAAATCC | 263 |
| 4 | GGGCTACGTTTCATTTGTATG | GCAACCTATTCTTAAAGCATAAGACTG | 355 |
| 5 | AGGCTCTTTGTACCTACAGC | CATGTAGGGTCCGTCTCATT | 199 |
| 6 | CACACGTGTTAAGTCTTCATAGT | AGCCCCTCAAGTATTTATCCT | 394 |
| 7 | GAACCTGACCTTCCTGTTCTC | GTTGGCTGTTATCTTCAGTTTC | 241 |
| 8 | GACTAGGCAATATCATAGCATAG | CTTTCTACTATATTATCATCCGG | 320 |

TABLE 2-continued

Primer Sequences Used for Mutation Analysis of SCN1A

| Exon | Forward Primer | Reverse Primer | Size (bp) |
|---|---|---|---|
| 9 | TTGAAAGTTGAAGCCACCAC | CCACCTGCTCTTAGGTACTC | 363 |
| 10 | GCCATGCAAATACTTCAGCCC | CACAACAGTGGTTGATTCAGTTG | 480 |
| 11a | TGAATGCTGAAATCTCCTTCTAC | CTCAGGTTGCTGTTGCGTCTC | 306 |
| 11b | GATAACGAGAGCCGTAGAGAT | TCTGTAGAAACACTGGCTGG | 315 |
| 12 | CATGAAATTCACTGTGTCACC | CAGCTCTTGAATTAGACTGTC | 347 |
| 13a | ATCCTTGGGAGGTTTAGAGT | CATCACAACCAGGTTGACAAC | 292 |
| 13b | CTGGGACTGTTCTCCATATTG | GCATGAAGGATGGTTGAAAG | 277 |
| 14 | CATTGTGGGAAAATAGCATAAGC | GCTATGCAGAACCCTGATTG | 338 |
| 15a | TGAGACGGTTAGGGCAGATC | AGAAGTCATTCATGTGCCAGC | 348 |
| 15b | CTGCAAGATCGCCAGTGATTG | ACATGTGCACAATGTGCAGG | 276 |
| 16a | GTGGTGTTTCCTTCTCATCAAG | TCTGCTGTATGATTGGACATAC | 387 |
| 16b | CAACAGTCCTTCATTAGGAAAC | ACCTTCCCACACCTATAGAATC | 353 |
| 17 | CTTGGCAGGCAACTTATTACC | CAAGCTGCACTCCAAATGAAAG | 232 |
| 18 | TGGAAGCAGAGACACTTTATCTAC | GTGCTGTATCACCTTTTCTTAATC | 234 |
| 19 | CCTATTCCAATGAAATGTCATATG | CAAGCTACCTTGAACAGAGAC | 318 |
| 20 | CTACACATTGAATGATGATTCTGT | GCTATATACAATACTTCAGGTTCT | 216 |
| 21a | ACCAGAGATTACTAGGGGAAT | CCATCGAGCAGTCTCATTTCT | 303 |
| 21b | ACAACTGGTGACAGGTTTGAC | CTGGGCTCATAAACTTGTACTAAC | 297 |
| 22 | ACTGTCTTGGTCCAAAATCTG | TTCGATTAATTTTACCACCTGATC | 267 |
| 23 | AGCACCAGTGACATTTCCAAC | GGCAGAGAAAACACTCCAAGG | 272 |
| 24 | GACACAGTTTTAACCAGTTTG | TGTGAGACAAGCATGCAAGTT | 207 |
| 25 | CAGGGCCAATGACTACTTTGC | CTGATTGCTGGGATGATCTTGAATC | 477 |
| 26a | CGCATGATTTCTTCACTGGTTGG | GCGTAGATGAACATGACTAGG | 247 |
| 26b | TCCTGCGTTGTTTAACATCGG | ATTCCAACAGATGGGTTCCCA | 288 |
| 26c | TGGAAGCTCAGTTAAGGGAGA | AGCGCAGCTGCAAACTGAGAT | 261 |
| 26d | CCGATGCAACTCAGTTCATGGA | GTAGTGATTGGCTGATAGGAG | 274 |
| 26e | AGAGCGATTCATGGCTTCCAATCC | TGCCTTCTTGCTCATGTTTTCCACA | 335 |
| 26f | CCTATGACCGGGTGACAAAGCC | TGCTGACAAGGGGTCACTGTCT | 242 |

Note:
Primer sequences are listed 5' to 3'. Due to the large size of exons 11, 13, 15, 16, 21 and 26, the exons were split into two or more overlapping amplicons.

TABLE 3

SCN1A Polymorphisms Identified

| Position | SCN1A polymorphism | | Frequency (%) | |
| --- | --- | --- | --- | --- |
| | Mutation | Amino acid change | GEFS+ | Normal |
| Intron 13 | IVS13 − 14 37C > A | — | 2.4 | 8.6 |
| Exon 14 | c.2522C > G | — | 2.4 | 8.6 |
| Inron 15 | IVS15 + 54A > G | — | 36.3 | 23.6 |
| Exon 15 | c.2889T > C | — | 1.2 | 0.0 |
| Exon 16 | c.3199G > A | T1067A | 29.5 | 30.8 |
| Exon 26 | c.5782C > G | R1928G | 1.2 | 1.7 |

Note
Total GEFS + samples = 53;
Total normal sa

EXAMPLE 6

Identification of Mutations in Ion Channels

Human genomic sequence available from the Human Genome Project was used to characterize the genomic organisation for each sodium channel subunit gene. Each gene was subsequently screened for sequence changes using single strand conformation polymorphism (SSCP) analysis in a large sample of epileptics with common sporadic IGE subtypes eg juvenile myoclonic epilepsy (JME), childhood absence epilepsy (CAE), juvenile absence epilepsy (JAE) and epilepsy with generalized tonic-clonic seizures (TCS). Clinical observations can then be compared to the molecular defects characterized in order to establish the combinations of mutant subunits involved in the various disease states, and therefore to provide validated drug targets for each of these disease states. This will provide a basis for novel drug treatments directed at the genetic defects present in each patient.

The coding sequence for each of the ion channel subunits was aligned with human genomic sequence present in available databases at the National Centre for Biotechnology Information (NCBI). The BLASTN algorithm was typically used for sequence alignment and resulted in the genomic organisation (intron-exon structure) of each gene being determined. Where genomic sequence for an ion channel subunit was not available, BACs or PACs containing the relevant ion channel subunit were identified through screening of high density filters containing these clones and were subsequently sequenced.

Availability of entire genomic sequence for each ion channel subunit facilitated the design of intronic primers spanning each exon. These primers were used for both high throughput SSCP screening and direct DNA sequencing.

EXAMPLE 7

Sample Preparation for SSCP Screening

A large collection of individuals affected with epilepsy have undergone careful clinical phenotyping and additional data regarding their family history has been collated. Informed consent was obtained from each individual for blood collection and its use in subsequent experimental procedures. Clinical phenotypes incorporated classical IGE cases as well as GEFS+ and febrile seizure cases.

DNA was extracted from collected blood using the QIAamp DNA Blood Maxi kit (Qiagen) according to manufacturers specifications or through procedures adapted from Wyman and White (1980). Stock DNA samples were kept at a concentration of 1 ug/ul.

In preparation for SSCP analysis, samples to be screened were formatted into 96-well plates at a concentration of 30 ng/ul. These master plates were subsequently used to prepare exon specific PCR reactions in the 96-well format.

EXAMPLE 8

Identification of Sequence Alterations in Ion Channel Genes

SSCP analysis of specific ion channel exons followed by sequencing of SSCP bandshifts was performed on individuals constituting the 96-well plates to identify sequence alterations.

Primers used for SSCP were labelled at their 5' end with HEX and typical PCR reactions were performed in a total volume of 10 µl. All PCR reactions contained 67 mM Tris-HCl (pH 8.8); 16.5 mM $(NH_4)_2SO_4$; 6.5 µM EDTA; 1.5 mM $MgCl_2$; 200 µM each DNTP; 10% DMSO; 0.17 mg/ml BSA; 10 mM β-mercaptoethanol; 5 µg/ml each primer and 100 U/ml Taq DNA polymerase. PCR reactions were performed using 10 cycles of 94° C. for 30 seconds, 60° C. for 30 seconds, and 72° C. for 30 seconds followed by 25 cycles of 94° C. for 30 seconds, 55° C. for 30 seconds, and 72° C. for 30 seconds. A final extension reaction for 10 minutes at 72° C. followed.

Twenty µl of loading dye comprising 50% (v/v) formamide, 12.5 mM EDTA and 0.02% (w/v) bromophenol blue were added to completed reactions which were subsequently run on non-denaturing 4% polyacrylamide gels with a cross-linking ratio of 35:1 (acrylamide:bis-acrylamide) and containing 2% glycerol. Gel thickness was 100 µm, width 168 mm and length 160 mm. Gels were run at 1200 volts and approximately 20 mA, at 22° C. and analysed on the GelScan 2000 system (Corbett Research, Australia) according to manufacturers specifications.

PCR products showing a conformational change were subsequently sequenced. This first involved re-amplification of the amplicon from the relevant individual (primers used in this instance did not contain 5' HEX labels) followed by purification of the PCR amplified templates for sequencing using QiaQuick PCR preps (Qiagen) based on manufacturers procedures. The primers used to sequence the purified amplicons were identical to those used for the initial amplification step. For each sequencing reaction, 25 ng of primer and 100 ng of purified PCR template were used. The BigDye sequencing kit (ABI) was used for all sequencing reactions according to the manufacturers specifications. The products were run on an ABI 377 Sequencer and analysed using the EditView program.

Table 4 shows the novel sequence changes identified in the ion channel subunits to date.

EXAMPLE 9

Digenic Model Examples

In some instances a single mutation in an ion channel alone is insufficient to give rise to an epilepsy phenotype. However combinations of mutations each conferring a subtle change of function to an ion channel, as proposed by the digenic model (PCT/AU01/00872), may be sufficient to produce an epilepsy phenotype.

Using the mutations and variations in ion channel subunits that form part of this invention, the digenic model may be validated through a parametric analysis of large families in which two abnormal alleles co-segregate by chance to identify mutations which act co-operatively to give an epilepsy phenotype. It is envisaged that the strategy of careful clinical phenotyping in these large families, together with a linkage analysis based on the digenic hypothesis will allow identification of the mutations in ion channels associated with IGEs. If molecular genetic studies in IGE are successful using the digenic hypothesis, such an approach might serve as a model for other disorders with complex inheritance.

The digenic hypothesis predicts that the closer the genetic relationship between affected individuals, the more similar the sub-syndromes, consistent with published data (Italian League Against Epilepsy Genetic Collaborative Group, 1993). This is because more distant relatives are less likely to share the same combinations of mutated subunits.

Identical twins have the same pair of mutated subunits and the same minor alleles so the sub-syndromes are identical. Affected sib-pairs, including dizygous twins, with the same sub-syndrome would also have the same pair of mutated subunits, but differences in minor alleles would lead to less similarity than with monozygous twins. Some sib-pairs and dizygous twins, have quite different sub-syndromes; this would be due to different combinations of mutated subunits, when the parents have more than two mutated alleles between them.

A special situation exists in inbred communities that parallels observations on autosomal recessive mouse models. Here the two mutated alleles of the digenic model are the same and thus result in a true autosomal recessive disorder. Because all affected individuals have the same pair of mutated alleles, and a similar genetic background, the phenotypes are very similar.

In outbred communities approximately 1% of the population would have IGE genotypes (2 mutated alleles) and 0.3% would clinically express IGE. Most of these would have mutations in two different channel subunits. In such communities most cases would appear "sporadic" as the risk to first degree relatives would be less than 10%.

For example, let there be three IGE loci (A,B,C) and let the frequency of abnormal alleles (a*,b*,c*) at each locus be 0.027 and of normal alleles (a, b, c) be 0.973. Then, the distribution of genotypes aa*, a*a, a*a* and aa at locus A will be 0.0263 (0.027×0.973), 0.0263, 0.0007 and 0.9467 respectively, and similarly for loci B and C. In this population 0.8485 will have no mutated alleles ($0.9467^3$), 0.1413 will have one mutated allele (a* or b* or c*; $0.0263 \times 0.9467^2 \times 6$), 0.0098 will have two abnormal alleles (0.0020 two same abnormal alleles, 0.0078, two different abnormal alleles) and 0.00037 will have more than two abnormal alleles. Thus in this population 0.01, or 1%, will have two or more abnormal alleles (IGE genotype), and the total abnormal allele frequency will be 0.08 (3×0.027).

To determine the familial risks and allele patterns in affected pairs, the frequency distribution of population matings and the percentage of children with 2 or more abnormal alleles must be determined. The frequency of matings with no abnormal alleles (0×0) is 0.72 ($0.8485^2$), for 1×0 and 0×1 matings 0.24 (2×0.8485×0.1413), for a 1×1 mating 0.020, and for 2×0 and 0×2 matings 0.0166 etc. From this distribution of matings the frequency of children with 2 or more abnormal alleles can be shown to be 0.01. For example, the 0×2 and 2×0 matings contribute 0.0033 of this 0.01 frequency (0.0166 [mating frequency]×0.2 [chance of that mating producing a child with 2 or more abnormal alleles]).

To determine parental risk it can be shown that of children with 2 abnormal alleles (IGE genotype), 0.49 derive from 1×1 matings where no parent is affected, 0.33 derive from a 2×0 and 0×2 matings etc. For the 2×0 and 0×2 matings, half the parents have IGE genotypes and contribute 0.16 (0.33/2) to the parental risk with the total parental risk of an IGE genotype being 0.258. The other matings that contribute to affected parent-child pairs are 2×1, 1×2, 3×0, 0×3 etc.

The sibling risk of an IGE genotype is 0.305. For example 2×0 and 0×2 matings contributed 0.08 to the sibling risk (0.33[fraction of children with 2 abnormal alleles]×0.25[the chance of that mating producing a child with 2 or more abnormal alleles]). Similarly the offspring risk was determined to be 0.248 by mating individuals with 2 abnormal alleles with the general population. Thus at 30% penetrance the risk for IGE phenotype for parents of a proband is 0.077, for siblings 0.091, and for offspring 0.074.

It can be shown that affected sib pairs share the same abnormal allele pair in 85% of cases. This is because of all affected sib pairs 44% derive from 1×1 matings and 23% from 0×2 and 2×0 matings where all affected siblings have the same genotype. In contrast, 24% derive from 1×2 matings and 9% from 3×1 and 2×2 matings etc where affected sibling genotypes sometimes differ.

For affected parent-child pairs, genotypes are identical in only 58%. Of affected parent child pairs, 43% derive from 0×2 matings where gentoypes are identical, whereas 38% derive from 0×3 and 17% from 1×2 where the majority of crosses yield different affected genotypes.

Based on the digenic model it has been postulated that most classical IGE and GEFS$^+$ cases are due to the combination of two mutations in multi-subunit ion channels. These are typically point mutations resulting in a subtle change of function. The critical postulate is that two mutations, usually, but not exclusively, in different subunit alleles ("digenic model"), are required for clinical expression of IGE.

The hypothesis that similar phenotypes can be caused by the combination of mutations in two (or more) different subunits (outbred communities), or by the same mutation in two (or more) alleles of the same subunit (inbred communities), may seem implausible. However, applying the digenic hypothesis to the theoretical pentameric channel shown in FIG. 1, in outbred communities IGE will be due to subunit combinations such as $\alpha^*\alpha\beta^*\beta\Delta$, $\alpha^*\alpha\beta\beta\Delta^*$ or $\alpha\alpha\beta^*\beta\Delta^*$ (mutated subunits indicated by *). In inbred communities $\alpha^*\alpha^*\beta\beta\Delta$ or $\alpha\alpha\beta^*\beta^*\Delta$ combinations might cause IGE phenotypes. We assume that the mutations will not cause reduced expression of the alleles and that the altered ion channel excitability, and consequent IGE phenotype, caused by mutations in two different alleles is similar to that caused by the same mutation in both alleles of one subunit. Finally, subunit mutations with more severe functional consequences (eg breaking a disulphide bridge in SCN1B or amino acid substitution in the pore forming regions of SCN1A for GEFS$^+$) cause autosomal dominant generalized epilepsies with a penetrance of 60-90%. Such "severe" mutations are rare (allele frequency <0.01%) and are infrequent causes of GEFS$^+$. They very rarely, or perhaps never, cause classical IGE.

The relative separate segregation of classical IGE and GEFS$^+$ phenotypes is an anecdotal clinical observation of ours (Singh et al., 1999), although the separation is not absolute. The separation is supported by previous family and EEG studies of Doose and colleagues who described "type A" and "type B" liabilities which we may approximate the GEFS$^+$ and classical IGE groupings respectively (Doose and Baier, 1987).

The digenic model predicts that affected sib pairs will share the same genes in 85% of cases whereas they will have at least one different allele in the remaining 15%. In contrast, only 58% of parent-child pairs share the same alleles in a 3 locus model. Thus there should be greater similarity of syndromes between sibling pairs than parent-child pairs. This would be most objectively measured by age of onset and seizure types.

Estimates for the risk of febrile seizures or IGE in relatives vary. The estimates range from 5%-10% for siblings, 4%-6% for offspring, 3%-6% for parents, and 2-3% for grandparents. Underestimation may occur because IGE manifest in youth, and parents and particularly grandparents may be unaware of seizures in themselves in younger years. This is particularly true where there was stigma associated with epilepsy and where the epilepsy may have been mild and unrecognized. Underestimation of sibling and offspring risks occurs when unaffected young children are counted, some of whom will develop IGE in adolescence. Overestimation may occur with misdiagnosis of seizures or inclusion of seizures unrelated to IGE (e.g. due to trauma or tumors)

In autosomal dominant models the risk to affected relatives reduces proportionally (50% for first degree relatives, 25% for second degree etc). For all oligogenic or polygenic models the risk decreases more quickly. For a digenic model with three loci, the risks are 9.1% for siblings, 7.4% for offspring, 7.7% for parents. Rigorous measurement of the familial recurrence rates, with careful phenotyping and age-corrected risk estimates could be compared with the predictions from the digenic model, and it is proposed to do this.

There is a small amount of information on IGE families regarding haplotype distribution. For example, there is some evidence for a locus on 8q as determined by parametric linkage in a single family (Fong et al., 1998) and by non-parametric analysis in multiple small families (Zara et al., 1995). Interestingly, in the latter study the 8q haplotype not infrequently came from the unaffected parent. This would be quite compatible with the digenic model and evaluation of other data sets in this manner could be used to test the hypothesis, and it is proposed to do this.

Following the analysis of one large family with epilepsy where the two main phenotypes were childhood absence epilepsy (CAE) and febrile seizures (FS), the inheritance of FS was found to be autosomal: dominant and the penetrance 75%. However the inheritance of CAE in this family was not simple Mendelian, but suggestive of complex inheritance with the involvement of more than one gene. The power of this large family was used to explore the complex genetics of CAE further.

Linkage analysis on this family in which individuals with CAE, FS and FS+ were deemed affected led to the detection of linkage on chromosome 5q and identification of a mutation in the GABRG2 gene (R43Q) which is localised to this region (Wallace et al., 2001a; PCT/AU01/00729). All 10 tested individuals with FS alone in this family had this mutation and 7 CAE affected individuals in this family also had the mutation. To test the digenic model of IGEs in the CAE affected individuals, the whole genome screen of this family was reanalysed with only individuals with CAE considered affected. Linkage analysis was performed using FASTLINK v4.0, two-point lod scores were calculated assuming 50% penetrance and a 2% phenocopy rate and individuals with FS or FS+ were coded as unknown. Markers producing a lod score greater than 1 were reanalysed without a phenocopy rate and at the observed penetrance for CAE in this family (30%). Results from the analysis revealed significant linkage to chromosome 14q22-q23 (lod 3.4). This provides strong evidence for a second locus segregating with CAE affected individuals in this family. While the GABRG2 mutation is sufficient to cause FS, the CAE phenotype is thought to be due to both the GABRG2 mutation and a mutation occurring in a gene mapping to the 14q locus, as proposed by the digenic model.

Figure 5:
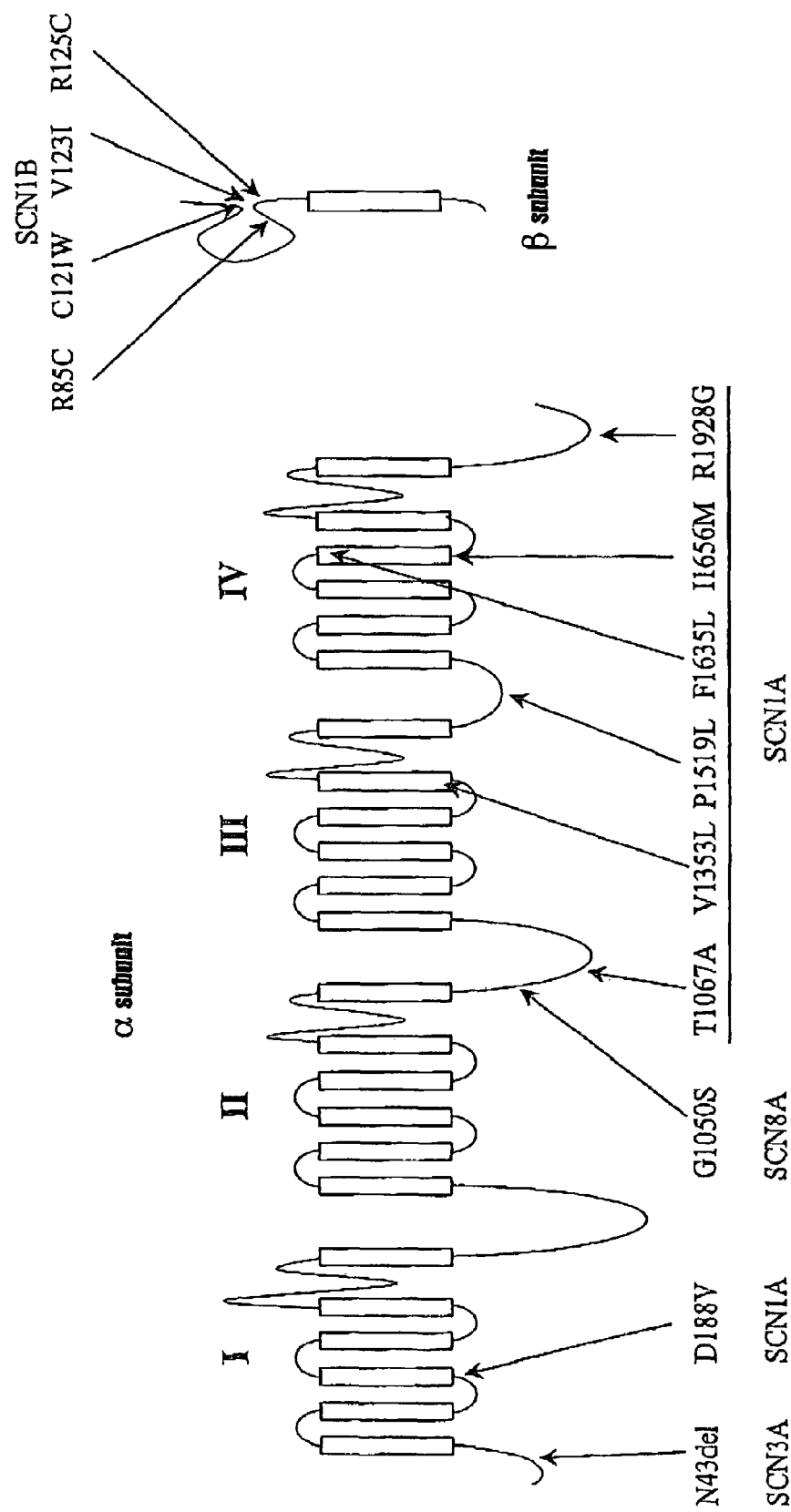
FIG. 5 represents the location of mutations identified in the ion channel subunits constituting the sodium channel. These examples include both novel and previously identified mutations.

For the application of the digenic model to sporadic cases of IGE and affected individuals belonging to smaller families in which genotyping and linkage analysis is not a feasible approach to disease gene identification, direct mutation analysis of ion channel genes in these individuals has been carried out as described above. In Table 4 there is provided an indication of novel genetic alterations so far identified through mutation analysis screening of these individuals. FIG. 5 provides an example to indicate where some of these mutations have occurred with respect to the sodium channel genes.

The identification of novel mutations and variations in ion channel subunits in IGE individuals provides resources to further test the digenic hypothesis and mutation profiles are starting to accumulate for a number of subunit changes that are observed in the same individuals. FIG. 6 provides results from some of these profiles.

FIG. 6A shows a 3 generation family in which individual III-1 has myoclonic astatic epilepsy and contains a N43del mutation in the SCN3A gene as well as an A1067T mutation in the SCN1A gene. Individual I-1 also has the SCN3A mutation but alone this mutation is not sufficient to cause epilepsy in this individual. The SCN3A mutation has likely been inherited from the grandfather through the mother, while the SCN1A mutation is likely to arise from the father. Both parents are unaffected but have yet to be screened for the presence of the mutations in these subunits. Individual II-1 is likely to contain an as yet unidentified ion channel subunit mutation acting in co-operation with the SCN3A mutation already identified in this individual.

FIG. 6B is another 3 generation family in which individual III-1 has myoclonic astatic epilepsy due to a combination of the same SCN3A and SCN1A mutations as above. However, in this family both parents have febrile seizures most likely due to the presence of just one of the mutations in each parent, as proposed by the model. This is in contrast to individuals II-2 and II-3 in FIG. 6A who also contain one of the mutations in these genes each. These individuals are phenotypically normal most likely due to incomplete penetrance of these mutations in each case.

FIG. 6C shows a larger multi-generation family in which individual IV-5 has a mutation in both the SCN3A and GABRG2 subunits. In combination, these give rise to severe myoclonic epilepsy of infancy but alone either cause febrile seizures (GABRG2 mutation in III-3 and IV-4) or are without an effect (SCN3A mutation in III-2) as proposed by the model.

These examples therefore illustrate the digenic model as determined from mutation analysis studies of ion channel subunits in affected individuals and highlight the need to identify genetic alterations in the genes encoding ion channel subunits.

TABLE 4

Examples of mutations and variations identified in sodium channel subunit genes

| Subunit Gene | Exon/Intron | DNA Mutation | Amino Acid Change | SEQ ID NOS |
|---|---|---|---|---|
| SCN1A[r] | Exon 1 | c111delC | P37fsX91 | 89, 119 |
| SCN1A[ra] | Exon 4 | c563A→T | D188V | |
| SCN1A[r] | Exon 9 | c1342-c1352del | I448X | 90, 120 |
| SCN1A[r] | Exon 20 | c3976G→C | A1326P | 91, 121 |
| SCN1A[r] | Exon 21 | c4057G→C | V1353L | |
| SCN1A[r] | Exon 24 | c4556C→T | P1519L | 92, 122 |
| SCN1A[r] | Exon 26 | c4905C→G | F1635L | 93, 123 |
| SCN1A[ra] | Exon 26 | c4968C→G | I1656M | |
| SCN1A[r] | Exon 26 | c5363-c5364ins | N1788fsX1796 | 94, 124 |
| SCN1A[r] | Exon 26 | c5536-c5539delAAAC | S1846fsX1856 | 95, 125 |
| SCN1A[r] | Exon 26 | c5643G→C | E1881D | 96, 126 |
| SCN1A[r] | Exon 26 | c5870A→G | E1957G | 97, 127 |
| SCN8A[r] | Exon 14 | c3148G→A | G1050S | 98, 128 |
| SCN1B[ra] | Exon 3 | c253C→T | R85C | |
| SCN1B[ra] | Exon 3 | c363C→G | C121W | |
| SCN1B[r] | Exon 3 | c367G→A | V123I | 99, 129 |
| SCN1B[r] | Exon 3 | c373C→T | R125C | 100, 130 |
| SCN2A[r] | Exon 21 | c3988C→T | L1330F | 101, 131 |
| SCN2A[r] | Exon 25 | c4687C→G | L1563V | 102, 132 |
| SCN2A[r] | Exon 26 | c5465C→T | A1822V | 103, 133 |
| SCN1A[ca] | Exon 16 | c3199A→G | T1067A | |
| SCN1A[ca] | Exon 26 | c5782C→G | R1928G | |
| SCN8A[c] | Exon 14 | c3076C→T | R1026C | 104, 134 |
| SCN3A[c] | Exon 1 | c127-129delAAT | N43del | 105, 135 |
| SCN1A[r] | Exon 15 | c2889T→C | — | |
| SCN3A[r] | Exon 13 | c1971G→A | — | 106 |
| SCN3A[r] | Exon 27 | c5511C→T | — | 107 |
| SCN1A[c] | Exon 14 | c2522C→G | — | |
| SCN1A[c] | Exon 26 | c5418C→A | — | 108 |
| SCN3A[c] | Exon 13 | c1884T→A | — | 109 |
| SCN3B[c] | Exon 3 | c438C→T | — | 110 |
| SCN1A[r] | Intron 8 | IVS8(-9-10)delTT | — | 111 |
| SCN1A[r] | Intron 10 | IVS10-47T→G | — | 112 |
| SCN1A[r] | Intron 18 | IVS18 + 1G→A | — | 113 |
| SCN1A[r] | Intron 22 | IVS22 – 14T→G | — | 114 |
| SCN8A[r] | Intron 6 | IVS6 + 9C→T | — | 115 |
| SCN3A[r] | Intron 23 | IVS23-31delT | — | 116 |
| SCN8A[c] | Intron 15 | IVS15 + 20G→A | — | 117 |
| SCN1B | Intron 1 | IVS1 + 15G→T | | 118 |
| SCN1A | Exon 5 | c664C→T | R222X | 136, 165 |
| SCN1A | Exon 8 | c1152G→A | W384X | 137, 166 |
| SCN1A | Exon 9 | c1183G→C | A395P | 138, 167 |
| SCN1A | Exon 9 | c1207T→C | F403L | 139, 168 |
| SCN1A | Exon 9 | c1237T→A | Y413N | 140, 169 |
| SCN1A | Exon 9 | c1265T→A | V422E | 141, 170 |
| SCN1A | Exon 21 | c4219C→T | R1407X | 142, 171 |
| SCN1A | Exon 26 | c5339T→C | M1780T | 143, 172 |
| SCN1A | Exon 26 | c5674C→T | R1892X | 144, 173 |
| SCN1B | Exon 3 | c254G→A | R85H | 145, 174 |
| SCN2A | Exon 6A | c668G→A | R223Q | 146, 175 |
| SCN2A | Exon 16 | c2674G→A | V892I | 147, 176 |
| SCN2A | Exon 17 | c3007C→A | L1003I | 148, 177 |
| SCN2A | Exon 19 | c3598A→G | T1200A | 149, 178 |
| SCN2A | Exon 20 | c3956G→A | R1319Q | 150, 179 |
| SCN2A | Exon 12 | c1785T→C | | 151 |
| SCN2A | Exon 27 | c4919T→A | | 152 |
| SCN1A | Intron 9 | IVS9 – 1G→A | | 153 |
| SCN1A | Intron 23 | IVS23 + 33G→A | | 154 |
| SCN2A | Intron 7 | IVS7 + 61T→A | | 155 |
| SCN2A | Intron 19 | IVS19 – 55A→G | | 156 |
| SCN2A | Intron 22 | IVS22 – 31A→G | | 157 |
| SCN2A | Intron 2 | IVS2 – 28G→A | | 158 |
| SCN2A | Intron 8 | IVS8 – 3T→C | | 159 |
| SCN2A | Intron 11 | IVS11 + 49A→G | | 160 |
| SCN2A | Intron 11 | IVS11 – 16C→T | | 161 |
| SCN2A | Intron 17 | IVS17 – 71C→T | | 162 |
| SCN2A | Intron 17 | IVS17 – 74delG | | 163 |
| SCN2A | Intron 17 | IVS17 – 74insG | | 164 |

References cited herein are listed on the following pages, and are incorporated herein by this reference.

Baulac S. et al. (1999). *Am. J. Hum. Genet.* 65: 1078-1085.
Bendahhou S. et al. (1999). *J. Neurosci.* 19: 4762-4771.
Cole, S P. et al. (1984). *Mol. Cell Biol.* 62: 109-120.
Cote, R J. et al. (1983). *Proc. Natl. Acad. Sci. USA* 80: 2026-2030.
Escayg A. et al. (2000). *Nature Genet.* 24: 343-345.
Goldman, C K. et al. (1997). *Nature Biotechnology* 15: 462-466.
Harlow, E. and Lane, D. (1988). *Antibodies: A Laboratory Manual* (Cold Spring Harbor Laboratory, Cold Spring Harbor, N.Y.).
Heller, R A. et al. (1997). *Proc. Natl. Acad. Sci. USA* 94: 2150-2155.
Huse, W D. et al. (1989). *Science* 246: 1275-1281.
Kohler, G. and Milstein, C. (1975). *Nature* 256: 495-497.
Kozbor, D. et al. (1985). *J. Immunol. Methods* 81:31-42.
Kuhn, F J P. and Greeff, N G. (1996). *J. Gen. Physiol.* 114: 167-183.
Lopes-Cendes I. et al. (2000). *Am. J. Hum. Genet.* 66: 698-701.
Moulard B. et al. (1999). *Am. J. Hum. Genet.* 65: 1396-1400.
Orlandi, R. et al. (1989). *Proc. Natl. Acad. Sci. USA* 86: 3833-3837.
Peiffer A. et al. (1999). *Ann. Neurol.* 46: 671-678.
Plummer N W. et al. (1998). *Genomics* 54: 287-296.
Plummer N W. and Meisler M H. (1999). *Genomics* 57: 323-331.
Sambrook, J. et al. (1989). *Molecular cloning: a laboratory manual.* Second Edition. (Cold Spring Harbour Laboratory Press, New York).
Scharf, D. et al. (1994). *Results Probl. Cell Differ.* 20: 125-162.
Scheffer I E. and Berkovic S F. (1997). *Brain* 120: 479-490.
Scheffer I E. et al. (2000). *Ann. Neurol.* 47: 840-841.
Schena, M. et al. (1996). *Proc. Natl. Acad. Sci. USA* 93: 10614-10619.
Singh R. et al. (1999). *Ann Neurol.* 45: 75-81.
Wallace R H. et al. (1998). *Nature Genet.* 19: 366-370.
Winter, G. et al. (1991). *Nature* 349: 293-299.
Andermann, E. (1982). *In: Genetic basis of the epilepsies*. Anderson, V E. Hauser, W A. Penry, J K. and Singh, C F. (Editors). New York, Raven Press. 355-374.
Annegers, J F. (1996). *The treatment of epilepsy: Principles and practice.* Second Edition. (Wyllie E (Ed) Williams and Wilkins).
Bell, J I. and Lathrop, M. (1996). *Nature Genet.* 13: 377-378.
Berkovic, S F. Andermann, F. Andermann, E. and Gloor, P. (1987). *Neurology* 37: 993-1000.
Berkovic, S F. Reutens, D C. Andermann, E. and Andermann, F. (1994). *In: Epileptic seizures and syndromes.* Wolf, P. (Editor). London: John Libbey. 25-37.
Berkovic, S F. Mazarib, A. Neufeld, M. et al. (2000). *Neurology* (Supplement 3). 54:A356.
Biervert, C. Schroeder, B C. Kubisch, C. Berkovic, S F. Propping, P. Jentsch, T J. and Steinlein, O K. (1998). *Science* 279: 403-406.
Cavazzuti, G B. Capella, L. and Nalin, A. (1980). *Epilepsia* 21: 43-55.
Charlier, C. Singh, N A. Ryan, S G. Lewis, T B. Reus, B E. Leach, R J. and Leppert, M. (1998). *Nature Genet.* 18: 53-55.
Cole, S P. Campling, B G. Atlaw, T. Kozbor, D. and Roder, J C. (1984). *Mol. Cell Biochem.* 62: 109-120.
Collins, F S. (1995). *Nature Genet.* 9: 347-350.
Commission on Classification and Terminology of the International League against Epilepsy. (1989). *Epilepsia* 30: 389-399.
Cote, R J. Morrissey, D M. Houghton, A N. Beattie, E J Jr. Oettgen, H F. and Old, L J. (1983). *Proc. Natl. Acad. Sci. USA* 80: 2026-2030.
Doose, H. and Baier, W K. (1987). *Neuropediatrics* 18 (Supplement 1): 1-64.
Doose, H. and Baier, W. (1989). *Clev. Clin. J. Med.* 56 (Supplement): s105-s110.
Dworakowska, B. and Dolowy, K. (2000). *Acta Biochim. Pol.* 47: 685-703.
Escayg, A. MacDonald, B T. Meisler, M H. Baulac, S. Huberfeld, G. An-Gourfinkel, I. Brice, A. LeGuern, E. Moulard, B. Chaigne, D. Buresi, C. and Malafosse, A. (2000). *Nature Genet.* 24: 343-345.
Fong, G C. Shah, P U. Gee, M N. Serratosa, J M. Castroviejo, I P. Khan, S. Ravat, S H. Mani, J. Huang, Y. Zhao, H Z. Medina, M T. Treiman, L J. Pineda, G. and Delgado-Escueta, A V. (1998). *Am. J. Hum. Genet.* 63: 1117-1129.
Gardiner, M. (2000). *J Neurol.* 247: 327-334.
Goldman, C K. Soroceanu, L. Smith, N. Gillespie, G Y. Shaw, W. Burgess, S. Bilbao, G. and Curiel, D T. (1997). *Nature Biotechnology* 15: 462-466.
Gonzalez, J E. et al. (1999). *Drug Discov. Today* 4: 431-439.
Greenberg, D A. Delagado-Escueta, A V. Maldonado, H M. and Widellitz, H. (1988a). *Genet Epidem.* 5: 81-94.
Greenberg, D A. Delgado-Escueta, A V. Widelitz, H. Sparkes, R S. Treiman, L. Maldonado, H M. Park, M S. and Terasaki, P I. (1988b). *Am. J. Med. Genet.* 31: 185-192.
Hamill, O P. et al. (1981). *Pflugers Arch.* 391: 85-100.
Hauser, W A. Annegers, J F. and Kurland, L T. (1993). *Epilepsia* 34: 453-468.
Heller, R A. Schena, M. Chai, A. Shalon, D. Bedilion, T. Gilmore, J. Woolley, D E. and Davis R W. (1997). *Proc. Natl. Acad. Sci. USA* 94: 2150-2155.
Huse, W D. Sastry, L. Iverson, S A. Kang, A S. Alting-Mees, M. Burton, D R. Benkovic, S J. and Lerner, R A. (1989). *Science* 246: 1275-1281.
Italian League Against Epilepsy Genetic Collaborative Group. (1993). *Epilepsia* 34: 819-26.
Janz, D. Beck-Mannagetta, G. and Sander, T. (1992). *Neurology* 42 (Supplement 5): 48-55.
Kohler, G. and Milstein, C. (1975). *Nature* 256: 495-497.
Kozbor, D. Abramow-Newerly, W. Tripputi, P. Cole, S P. Weibel, J. Roder, J C. and Croce, C M. (1985). *J. Immunol. Methods* 81:31-42.
Lernmark, A. and Ott, J. (1998). *Nature Genet.* 19: 213-214.
Okubo, Y. Matsuura, M. Asai, T. Asai, K. Kato, M. Kojima, T. and Toru, M. (1994). *Epilepsia* 35: 832-841.
Orlandi, R. Gussow, D H. Jones, P T. and Winter, G. (1989). *Proc. Natl. Acad. Sci. USA* 86: 3833-3837.
Panayiotopoulos, C P. and Obeid, T. (1989). *Ann. Neurol.* 25: 440-443.
Phillips, H A. Favre, I. Kirkpatrick, M. Zuberi, S M. Goudie, D. Heron, S E. Scheffer, I E. Sutherland, G R. Berkovic, S F. Bertrand, D. and Mulley, J C. (2001). *Am. J. Hum. Genet.* 68: 225-231.
Reutens, D C. and Berkovic, S F. (1995). *Neurology* 45: 1469-1476.
Risch, N. and Botstein, D. (1996). *Nature Genet.* 12: 351-353.
Roger, J. Bureau, M. Dravet, C. Dreifuss, F E. Perret, A. and Wolf, P. (1992). *Epileptic syndromes in infancy, childhood and adolescence.* 2nd Edition. London, John Libbey.
Scharf, K D. Materna, T. Treuter, E. and Nover, L. (1994). *Results Probl. Cell Differ.* 20: 125-162.

Scheffer, I E. and Berkovic, S F. (1997). *Brain* 120: 479-90.
Schena, M. Shalon, D. Heller, R. Chai, A. Brown, P O. and Davis, R W. (1996). *Proc. Natl. Acad. Sci. USA* 93: 10614-10619.
Singh, N A. Charlie, C. Stauffer, D. DuPont, B R. Leach, R J. Melis, R. Ronen, G M. Bjerre, I. Quattlebaum, T. Murphy, J V. McHarg, M L. Gagnon, D. Rosales, T O. Peiffer, A. Anderson, V E. and Leppert, M. (1998). *Nature Genet.* 18: 25-29.
Singh, R. Scheffer, I E. Crossland, K. and Berkovic, S F. (1999). *Ann. Neurol.* 45: 75-81.
Steinlein, O K. Mulley, J C. Propping, P. Wallace, R H. Phillips, H A. Sutherland, G R. Scheffer, I E. and Berkovic, S F. (1995). *Nature Genet.* 11: 201-203.
Todd, J A. (1999). *Lancet* 354 (Supplement 1): 15-16.
Wallace, R H. Marini, C. Petrou, S. Harkin, L A. Bowser, D N. Panchal, R G. Williams, D A. Sutherland, G R. Mulley, J C. Scheffer, I E. and Berkovic, S F. (2001a). *Nature Genet.* 28: 49-52.
Wallace, R H. Scheffer, I E. Barnett, S. Richards, M. Dibbens, L. Desai, R R. Lerman-Sagie, T. Lev, D. Mazarib, A. Brand, N. Ben-Zeev, B. Goikhman, I. Singh, R. Kremmidiotis, G. Gardner, A. Sutherland, G R. George, A L Jr. Mulley, J C. and Berkovic, S F. (2001b). *Am. J. Hum. Genet.* 68: 859-865.
Wallace, R H. Wang, D W. Singh, R. Scheffer, I. George, A. Phillips, H. Saar, K. Reis, A. Johnson, E. Sutherland, G. Berkovic, S. and Mulley, J. (1998). *Nature Genet.* 19: 366-370.
Winter, G. and Milstein, C. (1991). *Nature* 349: 293-299.
Wyman, A R. and White, R. (1980). *Proc. Natl. Acad. Sci.* 77: 6754-6758.
Zara, F. Bianchi, A. Avanzini, G. Di Donato, S. Castellotti, B. Patel, P I. and Pandolfo, M. (1995). *Hum. Mol. Genet.* 4: 1201-1207.
Zara, F. Gennaro, E. Stabile, M. Carbone, I. Malacarne, M. Majello, L. Santangelo, R. de Falco, F A. and Bricarelli, F D. (2000). *Am. J. Hum. Genet.* 66: 1552-1557.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07709225B2). An electronic copy of the "Sequence Listing" will also be available from the USPTO upon request and payment of the fee set forth in 37 CFR 1.19(b)(3).

---

The invention claimed is:

1. An isolated DNA comprising the sequence of SEQ ID NO: 101.

2. An expression vector comprising an isolated DNA molecule as claimed in claim 1.

3. An isolated cell transformed with an isolated DNA molecule as claimed in claim 1.

4. The isolated cell of claim 3, wherein the cell is an eukaryotic cell.

5. The isolated cell of claim 3, wherein the cell is a bacterial cell.

6. A method of preparing a polypeptide comprising the steps of:
   (1) culturing cells as claimed in claim 3 under conditions effective for polypeptide production; and
   (2) harvesting the polypeptide encoded by SEQ ID NO:101.

7. An isolated DNA comprising the sequence of SEQ ID NO: 142.

8. An expression vector comprising an isolated DNA molecule as claimed in claim 7.

9. An isolated cell transformed with an isolated DNA molecule as claimed in claim 7.

10. The isolated cell of claim 9, wherein the cell is an eukaryotic cell.

11. The isolated cell of claim 9, wherein the cell is a bacterial cell.

12. A method of preparing a polypeptide comprising the steps of:
   (1) culturing cells as claimed in claim 9 under conditions effective for polypeptide production; and
   (2) harvesting the polypeptide encoded by SEQ ID NO:142.

* * * * *